(12) United States Patent
Thatcher et al.

(10) Patent No.: US 10,888,545 B2
(45) Date of Patent: *Jan. 12, 2021

(54) COMPOSITIONS AND METHODS FOR TREATING ESTROGEN-RELATED MEDICAL DISORDERS

(71) Applicant: THE BOARD OF TRUSTEES OF THE UNIVERSITY OF ILLINOIS, Urbana, IL (US)

(72) Inventors: Gregory R. Thatcher, Chicago, IL (US); Debra Tonetti, Westchester, IL (US); Mary Ellen Molloy, Chicago, IL (US); Bradley Michalsen, Grayslake, IL (US); Zihui Qin, Mundelein, IL (US); Rui Xiong, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/885,273

(22) Filed: Jan. 31, 2018

(65) Prior Publication Data

US 2018/0214414 A1 Aug. 2, 2018

Related U.S. Application Data

(60) Continuation of application No. 15/264,407, filed on Sep. 13, 2016, now Pat. No. 9,895,348, which is a
(Continued)

(51) Int. Cl.
*G01N 33/574* (2006.01)
*A61K 31/381* (2006.01)
*C07D 333/64* (2006.01)

(52) U.S. Cl.
CPC .......... *A61K 31/381* (2013.01); *C07D 333/64* (2013.01); *G01N 33/57496* (2013.01);
(Continued)

(58) Field of Classification Search
None
See application file for complete search history.

(56) References Cited

U.S. PATENT DOCUMENTS

| | | | |
|---|---|---|---|
| 5,514,703 A | 5/1996 | Carlson et al. | |
| 5,596,106 A * | 1/1997 | Cullinan | A61K 31/34 549/468 |

(Continued)

FOREIGN PATENT DOCUMENTS

| | | |
|---|---|---|
| EP | 0827959 | 3/1998 |
| EP | 0905132 | 3/1999 |

(Continued)

OTHER PUBLICATIONS

Database Caplus Chemical Abstracts Service, Columbus, Ohio, US; Database Accession No. 1992:420038, Abstract of Von Angerer et al., Journal of Steroid Biochemistry and Molecular Biology (1992), 41(3-8), 557-62 (Year: 1992).*
(Continued)

*Primary Examiner* — Karl J Puttlitz
(74) *Attorney, Agent, or Firm* — Michael Best & Friedrich LLP

(57) ABSTRACT

Disclosed herein are methods for treatment of estrogen-related medical disorders. The methods of treatment may comprise administering to a subject in need of such treatment a composition comprising a therapeutically effective amount of at least one compound of formula (I)
(Continued)

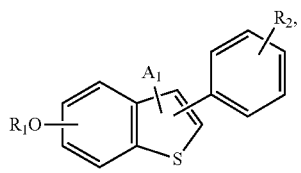

(I)

or a pharmaceutically acceptable salt thereof.

8 Claims, 10 Drawing Sheets

Related U.S. Application Data division of application No. 14/438,326, filed as application No. PCT/US2013/066699 on Oct. 24, 2013, now Pat. No. 9,475,791.

(60) Provisional application No. 61/808,971, filed on Apr. 5, 2013, provisional application No. 61/718,035, filed on Oct. 24, 2012.

(52) U.S. Cl.
CPC .............. *G01N 2333/91205* (2013.01); *G01N 2800/52* (2013.01)

(56) References Cited

U.S. PATENT DOCUMENTS

| 5,962,475 | A | 10/1999 | Schmid et al. |
| 5,994,547 | A | 11/1999 | Hoard et al. |
| 6,096,781 | A | 8/2000 | Cullinan |
| 6,291,484 | B1 | 9/2001 | Bryant et al. |
| 9,895,348 | B2 | 2/2018 | Thatcher et al. |
| 2011/0312925 | A1 | 12/2011 | Labrie |
| 2015/0284357 | A1 | 10/2015 | Thatcher et al. |
| 2015/0291552 | A1 | 10/2015 | Thatcher et al. |
| 2017/0114052 | A1 | 4/2017 | Thatcher et al. |

FOREIGN PATENT DOCUMENTS

| EP | 0920862 | | 6/1999 |
| EP | 1336602 | | 8/2003 |
| GB | 2459133 | * | 10/2009 |
| WO | WO 1995/010513 | | 4/1995 |
| WO | WO 1998/056812 | | 12/1998 |
| WO | WO 1999/025706 | | 5/1999 |
| WO | WO 2011/140198 | | 11/2011 |
| WO | WO 2014/066692 | | 5/2014 |
| WO | WO 2014/066695 | | 5/2014 |

OTHER PUBLICATIONS

Liu, Alzheimer's and Dementia, Jul. 2011, vol. 7, Issue 4, Supplement, p. S671 (Year: 2011).*
United States Patent Office Notice of Allowance for U.S. Appl. No. 15/382,338 dated Aug. 31, 2018 (10 pages).
Abdelhamid, R. et al., "Benzothiophene Selective Estrogen Receptor Modulators Provide Neuroprotection by a novel GPR30-dependent Mechanism," ACS Chem Neurosci, 2011, 2:256-268.
Abdul-Hay, S. et al., "NO-SSRIs: Nitric Oxide Chimera Drugs Incorporating a Selective Serotonin Reuptake Inhibitor," ACS Med Chem Lett, 2011, 2, 656.
Abdul-Hay, S.O. et al., "NO-flurbiprofen reduces amyloid-beta, is neuroprotective in cell culture, and enhances cognition in response to cholinergic blockade," J Neurochem, 2009, 111, 766.
Agnusdei, D. et al., "Raloxifene: results from the MORE study," J Musculoskelet Neuronal Interact, 2000, 1, 127.
Antonicelli, R. et al., "Prevention of cardiovascular events in early menopause: a possible role for hormone replacement therapy," Int J Cardiol, 2008, 130, 140.
Arlt, S. et al., "Dimethylarginines, homocysteine metabolism, and cerebrospinal fluid markers for Alzheimer's disease," J Alzheimers Dis, 2012, 31, 751.
Assender, J.W. et al., "Protein kinase C isoform expression as a predictor of disease outcome on endocrine therapy in breast cancer," Journal of Clinical Pathology, 2007, 60:1216-21.
Ba, F. et al., "The neuroprotective effects of estrogen in SK-N-SH neuroblastoma cell cultures," Neurochem Int, 2004, 44, 401.
Barrett-Connor, E. et al., "Effects of raloxifene on cardiovascular events and breast cancer in postmenopausal women," N Engl J Med, 2006, 355, 125.
Bartus, R.T. et al., "The cholinergic hypothesis of geriatric memory dysfunction," Science, 1982, 217, 408.
Bennet, B.M. et al., "Cognitive deficits in rats after forebrain cholinergic depletion are reversed by a novel NO mimetic nitrate ester," Neuropsychopharmacology, 2007, 32, 505.
Black, L.J. et al., "Raloxifene (LY139481 HCl) prevents bone loss and reduces serum cholesterol without causing uterine hypertrophy in ovariectomized rats," J Clin Invest, 1994, 93:63-9.
Block, "Products Subclass 13: 2,3-Dihydrothiophenes and Derivates," Section 33.1.13 in Science of Synthesis, vol. 33: Houben-Weyl Methods of Molecular Transformations, Molander, G. A. editor, 2007, 203-234.
Bradley et al., "Synergistic methodologies for the synthesis of 3-aroyl-2-arylbenzo[b]thiophene-based selective estrogen receptor modulators. Two concise syntheses of raloxifene," Tetrahedron Letters, 1999, 40(28):5155-5159.
Brinton, R.D., "The healthy cell bias of estrogen action: mitochondrial bioenergetics and neurological implications," Trends Neurosci, 2008, 31, 529.
Burke, T.W. et al., "Arzoxifene as therapy for endometrial cancer," Gynecol Oncol, 2003, 90:S40-6.
Buzdar, A. et al., "Phase II, randomized, double-blind study of two dose levels of arzoxifene inpatients with locally advanced or metastatic breast cancer," J Clin Oncol, 2003, 21:1007-14.
Cantara, S., "TAT-BH4 counteracts Abeta toxicity on capillary endothelium," FEBS Lett, 2007, 581, 702.
Carlson, L.E. et al., "Steroid hormones, memory and mood in a healthy elderly population," Psychoneuroendocrinology, 1998, 23, 583.
Castoria, G., et al., "PI3-kinase in concert with Src promotes the S-phase entry of oestradiol-stimulated MCF-7 cells," EMBO J, 2001, 20:6050-9.
Catherino, W.H. et al., "Increasing the number of tandem estrogen response elements increases the estrogenic activity of a tamoxifen analogue," Cancer Letters, 1995, 92:39-47.
Chan, Y.C. et al., "Raloxifene improves vascular reactivity in pressurized septal coronary arteries of ovariectomized hamsters fed cholesterol diet," Pharmacol Res, 2012, 65, 182.
Chisamore, M.J. et al., "Novel Antitumor Effect of Estradiol in Athymic Mice Injected with a T47D Breast Cancer Cell Line Overexpressing Protein Kinase Calpha," Clinical Cancer Research, 2001, 7:3156-65.
Ciriza, I. et al., "Selective estrogen receptor modulators protect hippocampal neurons from kainic acid excitotoxicity: differences with the effect of estradiol," J Neurobiol, 2004, 61, 209.
Clegg, N.J. et al., "ARN-509: A Novel Antiandrogen for Prostate Cancer Treatment," Cancer Research, 2012, 72:1494-503.
Cohen, F.J. et al., "Uterine effects of 3-year raloxifene therapy in postmenopausal women younger than age 60," Obstet Gynecol, 2000, 95, 104.
Colton, C.A. et al., "NO synthase 2 (NOS2) deletion promotes multiple pathologies in a mouse model of Alzheimer's disease," Proc Natl Acad Sci U S A, 2006, 103, 12867.
Delmas, P.D. et al., "Effects of raloxifene on bone mineral density, serum cholesterol concentrations, and uterine endometrium in postmenopausal women," N Engl J Med, 1997, 337, 1641.

(56) References Cited

OTHER PUBLICATIONS

Dempsey, E.C. et al., "Protein kinase C isozymes and the regulation of diverse cell responses," American Journal of Physiology—Lung Cellular and Molecular Physiology, 2000, 279:L429-L38.
Dennis, M.K. et al., "In vivo effects of a GPR30 antagonist," Nat Chem Biol, 2009, 5, 421.
Dorwald, "Side Reactions in Organic Synthesis," 2005, Wiley: VCH, Weinheim p. IX of Preface p. 1-16.
Dubal, D.B. et al., "Estradiol Modulates bcl-2 in Cerebral Ischemia: A Potential Role for Estrogen Receptors," J. Neurosci, 1999, 19, 6385.
Ellis, M.J. et al., "Lower-Dose vs High-Dose Oral Estradiol Therapy of Hormone Receptor-Positive, Aromatase Inhibitor-Resistant Advanced Breast Cancer," JAMA: The Journal of the American Medical Association, 2009, 302:774-80.
Fan, L. et al., "Estrogen affects levels of Bcl-2 protein and mRNA in medial amygdala of ovariectomized rats," J Neurosci Res, 2008, 86, 3655.
Ferlazzo, N. et al., "The 894G > T (Glu298Asp) variant in the endothelial NOS gene and MTHFR polymorphisms influence homocysteine levels inpatients with cognitive decline," Neuromolecular Med, 2011, 13, 167.
Figtree, G.A. et al., "Raloxifene acutely relaxes rabbit coronary arteries in vitro by an estrogen receptor-dependent and nitric oxide-dependent mechanism," Circulation, 1999, 100, 1095.
Fisher, B. et al., "Endometrial Cancer in Tamoxifen-Treated Breast Cancer Patients: Findings From the National Surgical Adjuvant Breast and Bowel Project (NSABP) B-14," Journal of the National Cancer Institute, 1994, 86:527-37.
Foxton, R.H. et al., "Tetrahydrobiopterin availability in Parkinson's and Alzheimer's disease; potential pathogenic mechanisms," Neurochem Res, 2007, 32, 751.
Fuchs-Young, R. et al., "Raloxifene is a tissue-selective agonist/antagonist that functions through the estrogen receptor," Ann N Y Acad Sci, 1995, 761:355-60.
Galea, L.A. et al., "Gonadal hormone modulation of hippocampal neurogenesis in the adult," Hippocampus, 2006, 16, 225.
Galea, L.A., "Gonadal hormone modulation of neurogenesis in the dentate gyrus of adult male and female rodents," Brain Res Rev, 2008, 57, 332.
Garthwaite, G. et al., "Signaling from blood vessels to CNS axons through nitric oxide," J Neurosci, 2006, 26, 7730.
Gibbs, R.B. et al., "Effects of raloxifene and estradiol on hippocampal acetylcholine release and spatial learning in the rat," Psychoneuroendocrinology, 2004, 29, 741.
Gibbs, R.B., "Estrogen therapy and cognition: a review of the cholinergic hypothesis," Endocr Rev, 2010, 31, 224.
Gibbs, R.B., "Long-term treatment with estrogen and progesterone enhances acquisition of a spatial memory task by ovariectomized aged rats," Neurobiol Aging, 2000, 21, 107.
Gkaliagkousi, E. et al., "Nitric oxide signalling in the regulation of cardiovascular and platelet function," Front Biosci, 2011, 16, 1873.
Goekoop, R. et al., "Raloxifene exposure enhances brain activation during memory performance in healthy elderly males; its possible relevance to behavior," NeuroImage, 2005, 25, 63.
Goekoop, R. et al., "Raloxifene Treatment Enhances Brain Activation during Recognition of Familiar Items: a Pharmacological fMRI Study in Healthy Elderly Males," Neuropsychopharmacology, 2005, 31, 1508.
Grese, T.A. et al., "Molecular determinants of tissue selectivity in estrogen receptor modulators," Proc Natl Acad Sci U S A, 1997, 94:14105-10.
Grese, T.A. et al., "Structure-activity relationships of selective estrogen receptor modulators: modifications to the 2-arylbenzothiophene core of raloxifene," J Med Chem, 1997, 40:146-67.
Grohe, C. et al., "17 Beta-estradiol regulates nNOS and eNOS activity in the hippocampus," Neuroreport, 2004, 15, 89.
Hammond, R. et al., "GPR30 is positioned to mediate estrogen effects on basal forebrain cholinergic neurons and cognitive performance," Brain Res, 2011, 1379, 53.
Hochner-Celnikier, D., "Pharmacokinetics of raloxifene and its clinical application," Eur J Obstet Gynecol Reprod Biol, 1999, 85:23-9.
Hopper, R.A. et al., "Tonic and phasic nitric oxide signals in hippocampal long-term potentiation," J Neurosci, 2006, 26, 11513.
Ingle, J., "Estrogen as therapy for breast cancer," Breast Cancer Res, 2002, 4:133-6.
Ingle, J.N. et al., "Randomized Clinical Trial of Diethylstilbestrol versus Tamoxifen in Postmenopausal Women with Advanced Breast Cancer," New England Journal of Medicine, 1981, 304:16-21.
Ingle, J.N., "Sequencing of Endocrine Therapy in Postmenopausal Women with Advanced Breast Cancer," Clinical Cancer Research, 2004, 10:362s-7s.
Jacobsen, D.E. et al., "Raloxifene improves verbal memory in late postmenopausal women: a randomized, double-blind, placebo-controlled trial," Menopause, 2009.
Jans, D.M. et al., "Processing of amyloid precursor protein as a biochemical link between atherosclerosis and Alzheimer's disease," Cardiovasc Hematol Disord Drug Targets, 2006, 6, 21.
Jeynes, B. et al., "Significant negative correlations between capillary expressed eNOS and Alzheimer lesion burden," Neurosci Lett, 2009, 463, 244.
Jordan, V.C. et al., "The St. Gallen Prize Lecture 2011: Evolution of long-term adjuvant anti-hormone therapy: consequences and opportunities," the Breast, 2011, 20, Supplement 3:S1-S11.
Kelly, M.J. et al., "Rapid actions of plasma membrane estrogen receptors," Trends in Endocrinology and Metabolism, 2001, 12:152-6.
Kennedy, B.J., "Massive estrogen administration in premenopausal women with metastatic breast cancer," Cancer, 1962, 15:641-8.
Khorram, O. et al., "Endometrial and myometrial expression of nitric oxide synthase isoforms in pre- and postmenopausal women," J Clin Endocrinol Metab, 1999, 84, 2226.
Kokiko, O.N. et al., "Administration of raloxifene reduces sensorimotor and working memory deficits following traumatic brain injury," Behav Brain Res, 2006, 170, 233.
Kramar, E.A. et al., "Cytoskeletal changes underlie estrogen's acute effects on synaptic transmission and plasticity," J Neurosci, 2009, 29, 12982.
Larson, J. et al., "Role of N-methyl-D-aspartate receptors in the induction of synaptic potentiation by burst stimulation patterned after the hippocampal theta-rhythm," Brain Res, 1988, 441, 111.
Larson, J.et al., "Alterations in synaptic transmission and long-term potentiation in hippocampal slices from young and aged PDAPP mice," Brain Res, 1999, 840, 23.
Leblanc, E.S. et al., "Hormone replacement therapy and cognition: systematic review and meta-analysis," JAMA, 2001, 285, 1489.
Lewis, J.S. et al., "Estrogen-induced apoptosis Ma breast cancer model resistant to long-term estrogen withdrawal," the Journal of Steroid Biochemistry and Molecular Biology. 2005;94:131-41.
Liu, H. et al., "Apoptotic Action of 17β-Estradiol in Raloxifene-Resistant MCF-7 Cells in Vitro and in Vivo," Journal of the National Cancer Institute, 2003, 95:1586-97.
Liu, H. et al., "Bioactivation of the selective estrogen receptor modulator desmethylated arzoxifene to quinoids: 4'-fluoro substitution prevents quinoid formation," Chem Res Toxicol, 2005, 18:162-73.
Liu, H. et al., "Chemical modification modulates estrogenic activity, oxidative reactivity, and metabolic stability in 4'F-DMA, a new benzothiophene selective estrogen receptor modulator," Chem Res Toxicol, 2006, 19:779-87.
Liu, H. et al., "Uterine peroxidase-catalyzed formation of diquinone methides from the selective estrogen receptor modulators raloxifene and desmethylated arzoxifene," Chem Res Toxicol, 2007, 20, 1676-84.
Lonne, G. et al., "PKCalpha expression is a marker for breast cancer aggressiveness," Molecular Cancer, 2010, 9:76.
Lønning, P.E. et al., "High-dose estrogen treatment in postmenopausal breast cancer patients heavily exposed to endocrine therapy," Breast Cancer Research and Treatment, 2001, 67:111-6.
Luiking, Y.C. et al., "Arginine de novo and nitric oxide production in disease states," Am J Physiol Endocrinol Metab, 2012, 303, E1177.

(56) References Cited

OTHER PUBLICATIONS

MacKay, H.J. et al., "Protein kinase C: a target for anticancer drugs?," Endocrine-Related Cancer, 2003, 10:389-96.
Maki, P.M. et al., "Hormone therapy and cognitive function," Hum Reprod Update 2009, 15, 667.
Maki, P.M. et al., "Longitudinal effects of estrogen replacement therapy on PET cerebral blood flow and cognition," Neurobiol Aging 2000, 21, 373.
Maki, P.M., "Hormone therapy and cognitive function: is there a critical period for benefit?," Neuroscience, 2006, 138, 1027.
Meyer, M.R. et al., "Deletion of G protein-coupled estrogen receptor increases endothelial vasoconstriction," Hypertension, 2012, 59, 507.
Mufson, E.J. et al., "Mild cognitive impairment: pathology and mechanisms," Acta Neuropathol, 2012, 123, 13.
Nilsen, J. et al., "Dual action of estrogen on glutamate-induced calcium signaling: mechanisms requiring interaction between estrogen receptors and src/mitogen activated protein kinase pathway," Brain Res, 2002, 930, 216.
Nilsen, J. et al., "Mechanism of estrogen-mediated neuroprotection: regulation of mitochondrial calcium and Bcl-2 expression," Proc Nail Acad Sci U S A, 2003, 100, 2842.
Oddo, S. et al., "Triple-transgenic model of Alzheimer's disease with plaques and tangles: intracellular Abeta and synaptic dysfunction," Neuron, 2003, 39, 409.
O'Regan, R.M. et al., "Effects of the Antiestrogens Tamoxifen, Toremifene, and ICI 182,780 on Endometrial Cancer Growth," Journal of the National Cancer Institute, 1998, 90:1552-8.
Osipo, C. et al., "Paradoxical Action of Fulvestrant in Estradiol-Induced Regression of Tamoxifen-Stimulated Breast Cancer," Journal of the National Cancer Institute, 2003, 95:1597-608.
Osipo, C. et al., "Reversal of tamoxifen resistant breast cancer by low dose estrogen therapy," the Journal of Steroid Biochemistry and Molecular Biology, 2005, 93:249-56.
Overk, C.R. et al., "Structure-activity relationships for a family of benzothiophene selective estrogen receptor modulators including raloxifene and arzoxifene," ChemMedChem, 2007, 2:1520-6.
Palkowitz, A.D. et al., "Discovery and synthesis of [6-hydroxy-3-[4-[2-(1-piperidinyl)ethoxy]phenoxy]-2-(4-hydroxyphenyl)]b enzo[b]thiophene: a novel, highly potent, selective estrogen receptor modulator," J Med Chem, 1997, 40:1407-16.
Parcellier, A. et al., "PKB and the mitochondria: AKTing on apoptosis," Cell Signal, 2008, 20, 21.
Peethambaram, P.P. et al., "Randomized trial of diethylstilbestrol vs. tamoxifen in postmenopausal women with metastatic breast cancer. An updated analysis," Breast Cancer Research and Treatment, 1999, 54:117-22.
Pietras, R.J. et al., "Membrane-Associated Estrogen Receptor Signaling Pathways in Human Cancers," Clinical Cancer Research, 2007, 13:4672-6.
Prossnitz, E.R. et al., "The G-protein-coupled estrogen receptor GPER in health and disease," Nat Rev Endocrinol, 2011, 7, 715.
Qin, Z. et al., "Benzothiophene selective estrogen receptor modulators with modulated oxidative activity and receptor affinity," J Med Chem, 2007, 50:2682-92.
Qin, Z. et al., "Design and synthesis of neuroprotective methylthiazoles and modification as NO-chimeras for neurodegenerative therapy," J Med Chem, 2012, 55, 6784.
Qin, Z. et al., "Structural modulation of oxidative metabolism in design of improved benzothiophene selective estrogen receptor modulators," Drug Metab Dispos, 2009, 37:161-9.
Resnick, S.M. et al., "Effects of estrogen replacement therapy on PET cerebral blood flow and neuropsychological performance," Horm Behav, 1998, 34, 171.
Resnick, S.M. et al., "Estrogen replacement therapy and longitudinal decline in visual memory. A possible protective effect?," Neurology, 1997, 49, 1491.
Ridnour, L. et al., "Nitric Oxide-Mediated Regulation of beta-Amyloid Clearance via Alterations of MMP-9/TIMP-1," J Neurochem, 2012, vol. 123, Issue 5, 736-749.
Rocca, W.A. et al., "Oophorectomy, menopause, estrogen, and cognitive aging the timing hypothesis," Neurodegener Dis, 2010, 7, 163.
Rossouw, J.E. et al., "Risks and benefits of estrogen plus progestin in healthy postmenopausal women: principal results From the Women's Health Initiative randomized controlled trial," JAMA, 2002, 288, 321.
Saita, A. et al., "Randomized, double-blind, placebo-controlled study on effects of raloxifene and hormone replacement therapy on plasma no concentrations, endothelin-1 levels, and endothelium-dependent vasodilation in postmenopausal women," Arterioscler Thromb Vasc Biol, 2001, 21, 1512.
Santen, R.J. et al., "Adaptive Hypersensitivity to Estrogen," Clinical Cancer Research, 2004, 10:337s-45s.
Sato, M. et al., "LY353381.HC1 a novel raloxifene analog with improved SERM potency and efficacy in vivo," J Pharmacol Exp Ther, 1998, 287, 1.
Schiefer, I.T. et al., "Furoxans (1,2,5-Oxadiazole-N-Oxides) as Novel NO Mimetic Neuroprotective and Procognitive Agents," J Med Chem, 2012, 55, 3076.
Selley, M.L., "Increased (E)-4-hydroxy-2-nonenal and asymmetric dimethylarginine concentrations and decreased nitric oxide concentrations in the plasma of patients with major depression," J Affect Disord, 2004, 80, 249.
Sherwin, B.B., "Estrogen therapy: is time of initiation critical for neuroprotection?," Nat Rev Endocrinol, 2009, 5, 620.
Shim, W-S. et al., "Estradiol Hypersensitivity and Mitogen-Activated Protein Kinase Expression in Long-Term Estrogen Deprived Human Breast Cancer Cells in Vivo," Endocrinology, 2000, 141:396-405.
Shumaker, S.A. et al., "The Women's Health Initiative Memory Study (WHIMS): a trial of the effect of estrogen therapy in preventing and slowing the progression of dementia," Control Clin Trials, 1998, 19, 604.
Simoncini, T. et al., "Nongenomic mechanisms of endothelial nitric oxide synthase activation by the selective estrogen receptor modulator raloxifene," Circulation, 2002, 105, 1368.
Siris, E. et al., "Effects of raloxifene on fracture severity in postmenopausal women with osteoporosis: results from the MORE study. Multiple Outcomes of Raloxifene Evaluation," Osteoporos Int, 2002, 13, 907.
Smith, A.R. et al., "Age-related changes in endothelial nitric oxide synthase phosphorylation and nitric oxide dependent vasodilation: evidence for a novel mechanism involving sphingomyelinase and ceramide-activated phosphatase 2A," Aging Cell, 2006, 5, 391.
Smith, S. et al., "A novel nitrate ester reverses the cognitive impairment caused by scopolamine in the Morris water maze," Neuroreport, 2000, 11, 3883.
Snyder, K.R. et al., "Raloxifene hydrochloride," Am J Health Syst Pharm, 2000, 57:1669-75, quiz 76-8.
Song, R.X-D. et al., "Apoptotic action of estrogen," Apoptosis, 2003, 8:55-60.
Song, R.X-D. et al., "Effect of Long-Term Estrogen Deprivation on Apoptotic Responses of Breast Cancer Cells to 17β-Estradiol," Journal of the National Cancer Institute, 2001, 93:1714-23.
Song, R.X-D. et al "Linkage of Rapid Estrogen Action to MAPK Activation by ERCE±-Shc Association and Shc Pathway Activation," Molecular Endocrinology, 2002, 16:116-27.
Sporn, M.B., "Arzoxifene: A promising new selective estrogen receptor modulator for clinical chemoprevention of breast cancer," Clinical Cancer Research, 2004, vol. 10, No. 16, pp. 5313-5315.
Steenland, K. et al., "Recent trends in Alzheimer disease mortality in the United States, 1999 to 2004," Alzheimer Dis Assoc Disord, 2009, 23, 165.
Sterniczuk, R. et al., "Characterization of the 3xTg-AD mouse model of Alzheimer's disease: part 2. Behavioral and cognitive changes," Brain Res, 2010, 1348, 149.
Stirone, C. et al., "Estrogen receptor activation of phosphoinositide-3 kinase, akt, and nitric oxide signaling in cerebral blood vessels: rapid and long-term effects," Mol Pharmacol, 2005, 67, 105.
Suh, N. et al., "Arzoxifene, a new selective estrogen receptor modulator for chemoprevention of experimental breast cancer," Cancer Res, 2001, 61:8412-5.

(56) References Cited

OTHER PUBLICATIONS

Taddei, S. et al., "Menopause is associated with endothelial dysfunction in women," Hypertension, 1996, 28, 576.
Tanapat, P. et al., "Estrogen Stimulates a Transient Increase in the Number of New Neurons in the Dentate Gyrus of the Adult Female Rat," J. Neurosci, 1999, 19, 5792.
Thatcher, G.R. et al., "Nitric oxide mimetic molecules as therapeutic agents in Alzheimer's disease," Curr Alzheimer Res, 2005, 2, 171.
Thatcher, G.R. et al., "NO chimeras as therapeutic agents in Alzheimer's disease," Curr Alzheimer Res, 2006, 3, 237.
Toader, V. et al.: "Nitrosation, nitration, and autoxidation of the selective estrogen receptor modulator raloxifene by nitric oxide, peroxynitrite, and reactive nitrogen/oxygen species", Chemical Research in Toxicology, vol. 16, No. 10, Jun. 9, 2003, pp. 1264-1276.
Tonetti, D.A. et al., "Elevated protein kinase C alpha expression may be predictive of tamoxifen treatment failure," Br J Cancer, 2003, 88:1400-2.
Tonetti, D.A. et al., "Stable transfection of protein kinase C alpha cDNA in hormone-dependent breast cancer cell lines," Br J Cancer, 2000, 83:782-91.
Tran, C. et al., "Development of a Second-Generation Antiandrogen for Treatment of Advanced Prostate Cancer," Science, 2009, 324:787-90.
Turner, R.T. et al., "Skeletal effects of estrogen," Endocr Rev, 1994, 15, 275.
Vogel, V.G. et al., "Effects of tamoxifen vs raloxifene on the risk of developing invasive breast cancer and other disease outcomes: the NSABP Study of Tamoxifen and Raloxifene (STAR) P-2 trial," JAMA, 2006, 295, 2727.
Wegesin, D.J. et al., "Effects of hormone replacement therapy and aging on cognition: evidence for executive dysfunction," Neuropsychol Dev Cogn B Aging Neuropsychol Cogn, 2007, 14, 301.
White, B.P. et al., "Raloxifene and estradiol-induced tumor regression in tamoxifen-resistant T47D:A18/PKCα is accompanied by ERα translocation to extranuclear sites (submitted)," Molecular Cancer Research, 2012.
Wu, T.W. et al., "17Beta-estradiol induced Ca2+ influx via L-type calcium channels activates the Src/ERK/cyclic-AMP response element binding protein signal pathway and BCL-2 expression in rat hippocampal neurons: a potential initiation mechanism for estrogen-induced neuroprotection," Neuroscience, 2005, 135, 59.
Wu, X. et al., "Raloxifene and estradiol benzoate both fully restore hippocampal choline acetyltransferase activity in ovariectomized rats," Brain Research, 1999, 847, 98.
Wyckoff, M.H. et al., "Plasma membrane estrogen receptors are coupled to endothelial nitric-oxide synthase through Galpha(i)," J Biol Chem, 2001, 276, 27071.
Yaffe, K. et al., "Cognitive function in postmenopausal women treated with raloxifene," N Engl J Med, 2001, 344, 1207.
Yaffe, K. et al., "Effect of Raloxifene on Prevention of Dementia and Cognitive Impairment in Older Women: The Multiple Outcomes of Raloxifene Evaluation (MORE) Randomized Trial," Am J Psychiatry, 2005, 162, 683.
Yaffe, K. et al., "Estrogen therapy in postmenopausal women: effects on cognitive function and dementia," JAMA, 1998, 279, 688.
Yao, K. et al., "Antitumor Action of Physiological Estradiol on Tamoxifen-stimulated Breast Tumors Grown in Athymic Mice," Clinical Cancer Research, 2000, 6:2028-36.
Yu, B. et al., "Structural modulation of reactivity/activity in design of improved benzothiophene selective estrogen receptor modulators: induction of chemopreventive mechanisms," Mol Cancer Ther, 2007, 6:2418-28.
Zhang, Q.G. et al., "C terminus of Hsc70-interacting protein (CHIP)-mediated degradation of hippocampal estrogen receptor-alpha and the critical period hypothesis of estrogen neuroprotection," Proc Nail Acad Sci U S A, 2011, 108, E617.
Zhang, Y. et al., "Estradiol-Induced Regression in T47D: A18/PKCα Tumors Requires the Estrogen Receptor and Interaction with the Extracellular Matrix," Molecular Cancer Research, 2009, 7:498-510.
Zhou, J. et al., "Effects of estrogen treatment on expression of brain-derived neurotrophic factor and cAMP response element-binding protein expression and phosphorylation in rat amygdaloid and hippocampal structures," Neuroendocrinology, 2005, 81, 294.
Zirka, "Catalytic hydrogenation of benzothiophene to 2,3-dihydrobenzothiophene," Reaction Kinetics and Catalysis Letters, 1983, 23(1-2):7-13.
International Search Report and Written Opinion for Application No. PCT/US2013/066699 dated Jan. 28, 2014 (13 pages).
International Search Report and Written Opinion for Application No. PCT/US2013/066702 dated Feb. 10, 2014 (12 pages).
European Search Report for Application No. 13848425.8 dated Jun. 15, 2016 (8 pages).
European Search Report for Application No. 13849663.3 dated Aug. 17, 2016 (7 pages).
United States Patent Office Action for U.S. Appl. No. 14/438,361 dated Jun. 28, 2016 (18 pages).
United States Patent Office Notice of Allowance for U.S. Appl. No. 14/438,326 dated Jun. 10, 2016 (7 pages).
Extended European Search Report for Application No. 13848425.8 dated Sep. 19, 2016 (13 pages).
United States Patent Office Action for U.S. Appl. No. 15/264,407 dated Feb. 24, 2017 (17 pages).
Extended European Search Report for Application No. 17158707.4 dated Apr. 7, 2017 (9 pages).
European Examination Report for Application No. 13848425.8 dated Jun. 7, 2017 (4 pages).
United States Patent Office Action for U.S. Appl. No. 15/382,338 dated Sep. 13, 2017 (17 pages).
United States Patent Office Notice of Allowance for U.S. Appl. No. 15/264,407 dated Oct. 5, 2017 (7 pages).
United States Patent Office Action for U.S. Appl. No. 15/382,338 dated Mar. 9, 2018 (8 pages).
European Patent Office Action for Application No. 17158707.4 dated Apr. 10, 2019 (4 pages).
United States Patent Office Notice of Allowance for U.S. Appl. No. 16/177,112 dated Jun. 13, 2019 (9 pages).
An, "Selective Estrogen Receptor Modulators," Asian Spine Journal, 2016, 10(4):787-791.
Gennari et al., "Selective estrogen receptor modulator (SERM) for the treatment of osteoporosis in postmenopausal women: focus on lasofoxifene," Clinical Interventions in Aging, 2010, 5:19-29.
"Selective Estrogen Receptor Modulators (SERM)" Online <https://www.iofbonehealth.org/selective-estrogen-receptor-modulators-serm> accessed Jun. 11, 2019.
Swaby et al., "SERMs for the treatment and prevention of breast cancer," Rev Endocr Metab Disord, 2007, 8:229-239.
Canadian Patent Office Action for Application No. 2,928,131 dated Jul. 28, 2020 (4 pages).

\* cited by examiner

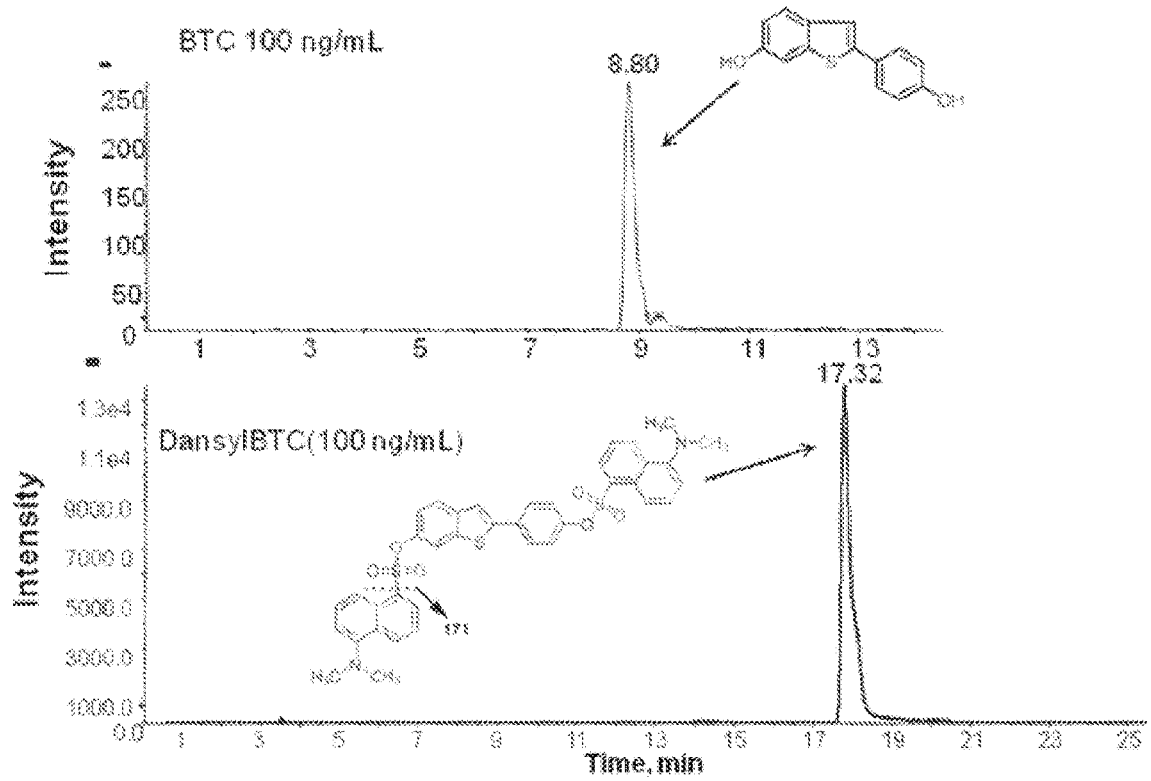
FIG. 6A
FIG. 6B
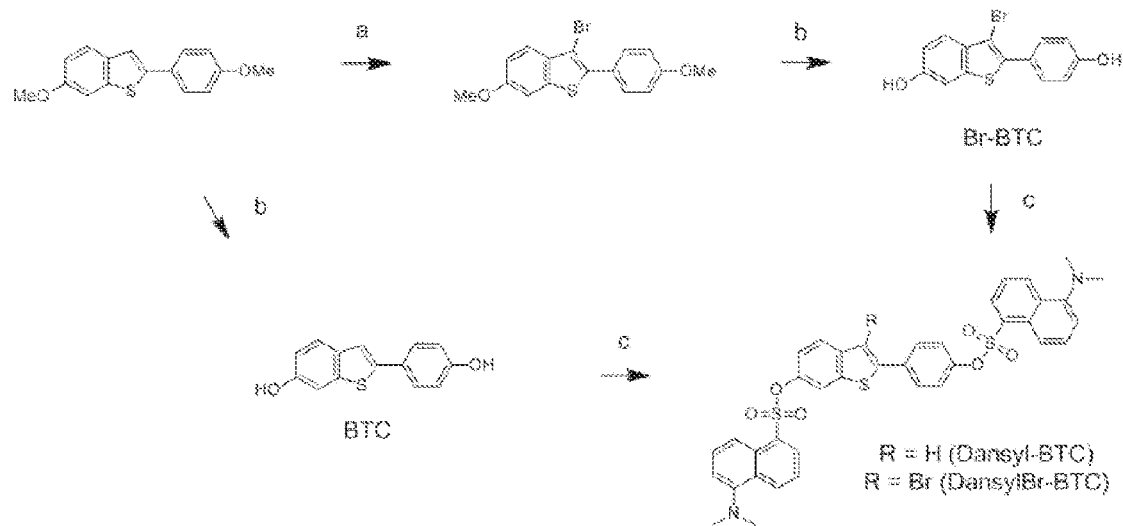
FIG. 7

Synthesis of TTC-352 and BM2-153 prodrugs

Reagents and conditions: (a) 4-methoxyphenol, NaH, DMF; (b) LiAlH$_4$, THF, 0 °C; (c) BBr$_3$, DCM, 0 °C Reagents and conditions: (a) POCl$_3$, NaOH, H$_2$O; (b) i. NaHDMS, THF, isobutyl sulfochloridate; ii. NaI, acetone; (c) EDCI, DIPEA, DMAP; (d) RCOCl or R-SO$_2$Cl, TEA, DCM

COMPOSITIONS AND METHODS FOR TREATING ESTROGEN-RELATED MEDICAL DISORDERS

CROSS-REFERENCE TO RELATED APPLICATION(S)

This is a continuation of U.S. patent application Ser. No. 15/264,407, filed on Sep. 13, 2016, which is a divisional of U.S. patent application Ser. No. 14/438,326, filed on Apr. 24, 2015, now U.S. Pat. No. 9,475,791, issued on Oct. 25, 2016, which is a U.S. national stage entry of International Patent Application No. PCT/US2013/066699, filed on Oct. 24, 2013, which claims priority to U.S. Provisional Patent Application No. 61/808,971, filed on Apr. 5, 2013, and U.S. Provisional Patent Application No. 61/718,035, filed on Oct. 24, 2012, the entire contents of all of which are fully incorporated herein by reference.

STATEMENT OF GOVERNMENT INTEREST

This invention was made with government support under grant numbers CA122914 and CA079870 awarded by the National Institutes of Health. The government has certain rights in the invention.

TECHNICAL FIELD

The present invention relates to compositions and methods for treating and identifying estrogen-related medical disorders such as cancer, inflammation, osteoporosis, vaginal atrophy, central nervous diseases, and cardiovascular system diseases.

BACKGROUND

The selective estrogen receptor modulator (SERM) tamoxifen (TAM) is the most widely prescribed endocrine therapy for the treatment and prevention of breast cancer. The development of resistance to TAM, either e novo or acquired, limits its clinical effectiveness, leading to disease progression. Before the introduction of TAM, breast cancer patients received high-dose 17β-estradiol (E2) or diethystilbesterol (DES) treatment. Although similar response rates were observed (9, 10), TAM treatment became the mainstay due to a lower incidence of side effects.

Protein kinase C α (PKCα) belongs to a family of serine/threonine protein kinases (1, 2). The expression of PKCα is associated with disease outcome for breast cancer patients on endocrine therapy. A shorter duration of response to endocrine therapy was associated with PKCα expression (3) and patients whose primary tumors overexpress PKCα were more likely to experience disease recurrence when treated with TAM (4). PKCα positivity is also associated with poor patient survival and breast cancer aggressiveness (5).

SUMMARY

Provided herein is a method for treatment of an estrogen-related medical disorder. The method may comprise administering to a subject in need of such treatment a composition comprising a therapeutically effective amount of at least one compound of formula (I)

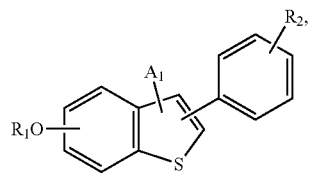

or a pharmaceutically acceptable salt thereof, wherein $R_1$ is selected from the group consisting of hydrogen, alkyl, $-SO_3R^{x1}$, $-PO_3R^{y1}R^{z1}$, and $-C(=O)R^a$;

$R_2$ is selected from the group consisting of halo and $-OR_3$;

$R_3$ is selected from the group consisting of hydrogen, alkyl, $-SO_3R^{x1}$, $-PO_3R^{y1}R^{x1}$, and $-C(=O)R^a$;

$A_1$ is H, alkyl, $-R^{b1}$, $-OR^{b2}$, or $-C(=O)R^{b3}$.

$R^{b1}$, $R^{b2}$, and $R^{b3}$ are each independently selected from the group consisting of is alkyl, cycloalkyl, and phenyl substituted with 1, 2, or 3 substituents independently selected from halo and $-OR_4$;

$R_4$ is selected from the group consisting of hydrogen, alkyl, $-SO_3R^{x1}$, $-PO_3R^{y1}R^{z1}$, and $-C(=O)R^a$;

$R^a$, at each occurrence, is independently selected from the group consisting of $-OH$ and alkyl; and $R^{x1}$, $R^{y1}$ and $R^{z1}$ are, at each occurrence, independently selected from the group consisting of hydrogen and a pharmaceutically acceptable cation;

provided that the compound of formula (I) contains at least one group selected from $-OR_3$ and $-OR_4$.

In certain embodiments, 2-(4-fluorophenyl)-3-(4-hydroxyphenoxy)benzo[b]thiophen-6-ol (HP-BTF) is excluded as a compound of formula (I).

In certain embodiments, the compound of formula (I) has formula (I-i), formula (I-ii), formula (I-iii), formula (I-iv), formula (I-v), or formula (I-vi),

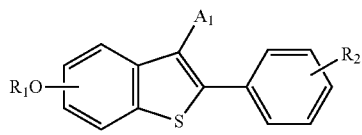

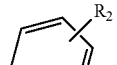

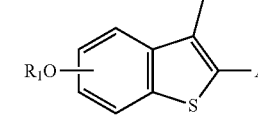

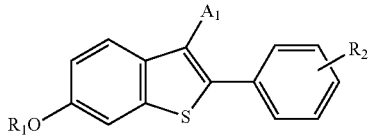

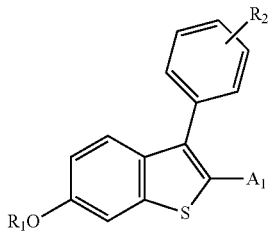
(I-iv)

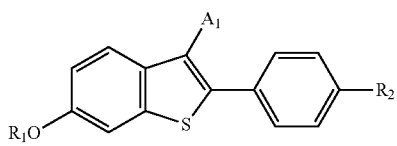
(I-v)

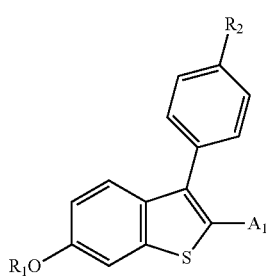
(I-vi)

wherein $R_1$, $R_2$, $R_3$, $A_1$, $R^{b1}$, $R^{b2}$, $R^{b3}$, $R_4$, $R^a$, $R^{x1}$, $R^{y1}$ and $R^{z1}$ are as defined above, and wherein the compounds of formula (I-i) through (I-vi) each contain at least one group selected from —OR$_3$ and —OR$_4$.

In certain embodiments, $R_1$ is hydrogen.

In certain embodiments, $R_2$ is halo. In certain embodiments, $R_2$ is fluoro. In certain embodiments, $R_2$ is —OR$_3$. In certain embodiments, $R_2$ is —OR$_3$, wherein $R_3$ is hydrogen.

In certain embodiments, $A_1$ is hydrogen. In certain embodiments, $A_1$ is —OR$^{b2}$. In certain embodiments, $A_1$ is —OR$^{b2}$, wherein $R^{b2}$ is phenyl substituted with 1, 2, or 3 substituents independently selected from halo and —OR$_4$. In certain embodiments, $A_1$ is —OR$^{b2}$, wherein $R^{b2}$ is phenyl substituted with 1 substituent independently selected from halo and —OR$_4$. In certain embodiments, $A_1$ is OR$^{b2}$, wherein $R^2$ is phenyl substituted with 1 substituent that is —OR$_4$. In certain embodiments, $A_1$ is —OR$^{b2}$, wherein $R^2$ is phenyl substituted with 1 substituent that is —OR$_4$, wherein $R_4$ is hydrogen.

In certain embodiments, $R_1$ is hydrogen; $R_2$ is —OR$_3$, wherein $R_3$ is hydrogen; and $A_1$ is hydrogen.

In certain embodiments, $R_1$ is hydrogen; $R_2$ is halo; and $A_1$ is —OR$^{b2}$, wherein $R^{b2}$ is phenyl substituted with 1 substituent that is —OR$_4$, wherein $R_4$ is hydrogen.

In certain embodiments, the compound of formula (I) has formula (I-vii)

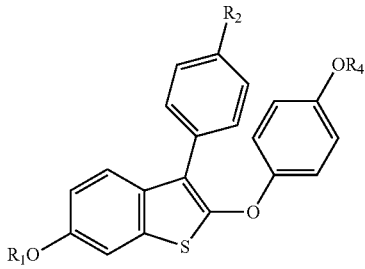
(I-vii)

wherein $R_1$, $R_2$, and $R_4$ are as defined above.

In certain embodiments, the compound of formula (I) has formula (I-viii)

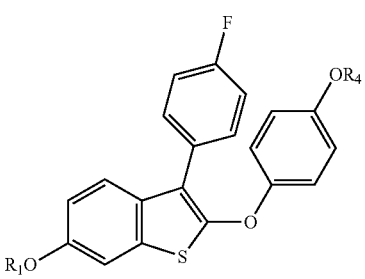
(I-viii)

wherein $R_1$ and $R_4$ are as defined above.

In certain embodiments, the compound of formula (I) has formula (I-ix)

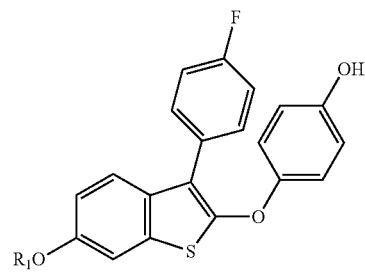
(I-ix)

wherein $R_1$ is as defined above. In certain embodiments, $R_1$ is selected from hydrogen and alkyl (e.g., $C_1$—, $C_2$—, $C_3$—, $C_4$—, $C_5$—, or $C_6$-alkyl).

In certain embodiments, the compound of formula (I) has formula (I-x), also referred to herein as TTC-352,

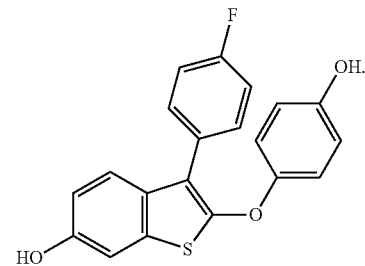
(I-x)

In certain embodiments, the compound of formula (I) is selected from the group consisting of:

2-(4-hydroxyphenyl)benzo[b]thiophen-6-ol (BTC);

3-(4-fluorophenyl)-2-(4-hydroxyphenoxy)benzo[b]thiophen-6-ol (TTC-352); and 4-((3-(4-fluorophenyl)-6-methoxybenzo[b]thiophen-2-yl)oxy)phenol (Monomethoxyl-TTC-352);

or a pharmaceutically acceptable salt thereof.

The estrogen-related medical disorder may be selected from the group consisting of: cancer, inflammation, osteoporosis, vaginal atrophy, central nervous system diseases, and cardiovascular system diseases. The central nervous system diseases may be selected from the group consisting of Alzheimer's Disease and mild cognitive impairment. The cancer may be selected from the group consisting of breast cancer, ovarian cancer, prostate cancer, and lung cancer. The breast cancer may be a tamoxifen resistant breast cancer or a triple negative breast cancer.

Also provided herein is a method of identifying a cancer in a subject. The method may comprise obtaining a test sample from the subject having cancer, and determining an amount of PKCα in the test sample. If the amount of PKCα in the test sample is greater than an amount of PKCα in a test sample from a subject not having cancer, then the cancer is sensitive to at least one compound of formula (I)

(I)

[structure of formula (I)]

or a pharmaceutically acceptable salt thereof,
wherein $R_1$ is selected from the group consisting of hydrogen, alkyl, —$SO_3R^{x1}$, —$PO_3R^{y1}R^{z1}$, and —$C(=O)R^a$;

$R_2$ is selected from the group consisting of halo and —$OR_3$;

$R_3$ is selected from the group consisting of hydrogen, alkyl, —$SO_3R^1$, —$PO_3R^{y1}R^{z1}$, and —$C(=O)R^a$;

$A_1$ is H, alkyl, —$R^{b1}$, —$OR^{b2}$, or —$C(=O)R^3$;

$R^{b1}$, $R^{b2}$, and $R^{b3}$ are each independently selected from the group consisting of is alkyl, cycloalkyl, and phenyl substituted with 1, 2, or 3 substituents independently selected from halo and —$OR_4$;

$R_4$ is selected from the group consisting of hydrogen, alkyl, —$SO_3R^{x1}$, —$PO_3R^{y1}R^{z1}$, and —$C(=O)R^a$;

$R^a$, at each occurrence, is independently selected from the group consisting of —OH and alkyl; and $R^{x1}$, $R^{y1}$ and $R^{z1}$ are, at each occurrence, independently selected from the group consisting of hydrogen and a pharmaceutically acceptable cation;

provided that the compound of formula (I) contains at least one group selected from —$OR_3$ and —$OR_4$.

In certain embodiments, 2-(4-fluorophenyl)-3-(4-hydroxyphenoxy)benzo[b]thiophen-6-ol (HP-BTF) is excluded as a compound of formula (I).

In certain embodiments, the compound of formula (I) has formula (I-i), formula (I-ii), formula (I-ii), formula (I-iv), formula(I-v), or formula (I-vi),

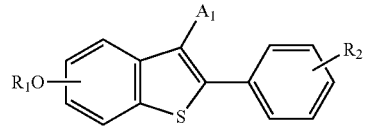

(I-i)

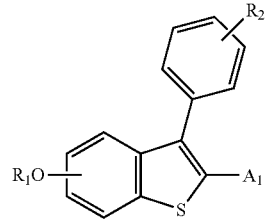

(I-ii)

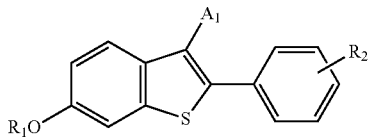

(I-iii)

(I-iv)

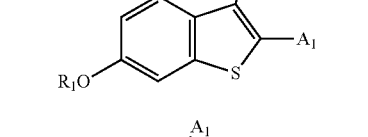

(I-v)

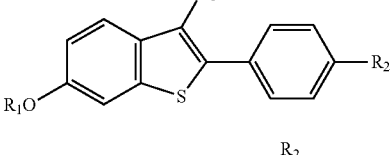

(I-vi)

wherein $R_1$, $R_2$, $R_3$, $A_1$, $R^{b1}$, $R^{b2}$, $R^{b3}$, $R_4$, $R^a$, $R^{x1}$, $R^{y1}$ and $R^{z1}$ are as defined above, and wherein the compounds of formula (I-i) through (I-vi) each contain at least one group selected from —$OR_3$ and —$OR_4$.

In certain embodiments, $R_1$ is hydrogen.

In certain embodiments, $R_2$ is halo. In certain embodiments, $R_2$ is fluoro. In certain embodiments, $R_2$ is —$OR_3$. In certain embodiments, $R_2$ is —$OR_3$, wherein $R_3$ is hydrogen.

In certain embodiments, $A_1$ is hydrogen. In certain embodiments, $A_1$ is —$OR^{b2}$. In certain embodiments, $A_1$ is —$OR^{b2}$, wherein $R^b$ is phenyl substituted with 1, 2, or 3 substituents independently selected from halo and —$OR_4$. In certain embodiments, $A_1$ is —$OR^{b2}$, wherein $R^b$ is phenyl substituted with 1 substituent independently selected from halo and —$OR_4$. In certain embodiments, At is —$OR^b$, wherein $R^{b2}$ is phenyl substituted with 1 substituent that is —OR$_4$. In certain embodiments, A$_1$ is —OR$^b$, wherein R$^{b2}$ is phenyl substituted with 1 substituent that is —OR$_4$, wherein R$_4$ is hydrogen.

In certain embodiments, R$_1$ is hydrogen; R$_2$ is —OR$_3$, wherein R$_3$ is hydrogen; and A$_1$ is hydrogen.

In certain embodiments, R$_1$ is hydrogen; R$_2$ is halo; and A$_1$ is —OR$^{b2}$, wherein R$^{b2}$ is phenyl substituted with 1 substituent that is —OR$_4$, wherein R$_4$ is hydrogen.

In certain embodiments, the compound of formula (I) has formula (I-vii)

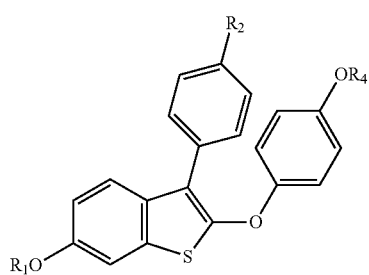

(I-vii)

wherein R$_1$, R$_2$, and R$_4$ are as defined above.

In certain embodiments, the compound of formula (I) has formula (I-viii)

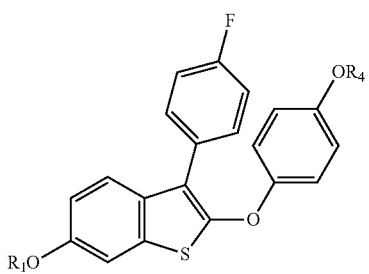

(I-viii)

wherein R$_1$ and R$_4$ are as defined above.

In certain embodiments, the compound of formula (I) has formula (I-ix)

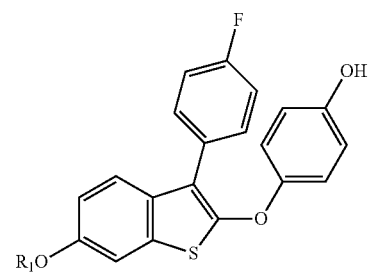

(I-ix)

wherein R$_1$ is as defined above. In certain embodiments, R$_1$ is selected from hydrogen and alkyl (e.g., C$_1$—, C$_2$—, C$_3$—, C$_4$—, C$_5$—, or C$_6$-alkyl).

In certain embodiments, the compound of formula (I) has formula (I-x), also referred to herein as TTC-352,

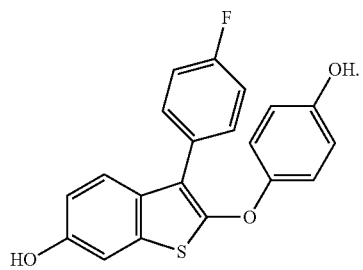

(I-x)

In certain embodiments, the compound of formula (I) is selected from the group consisting of:
2-(4-hydroxyphenyl)benzo[b]thiophen-6-ol (BTC);
3-(4-fluorophenyl)-2-(4-hydroxyphenoxy)benzo[b]thiophen-6-ol (TTC-352); and
4-((3-(4-fluorophenyl)-6-methoxybenzo[b]thiophen-2-yl)oxy)phenol (Monomethoxyl-TTC-352);
or a pharmaceutically acceptable salt thereof.

Further provided herein is a method for treatment of an estrogen-related medical disorder. The method may comprise administering to a subject in need of such treatment a composition comprising a therapeutically effective amount of at least one compound of formula (II)

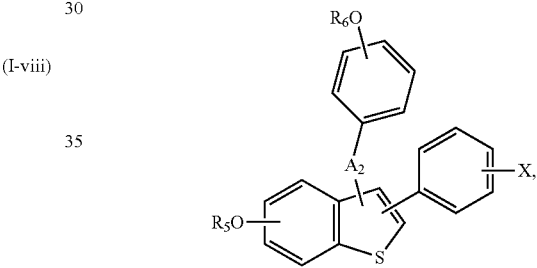

(II)

or a pharmaceutically acceptable salt thereof,
wherein
A$_2$ is —O— or —C(=O)—;
R$_5$ and R$_6$ are each independently selected from the group consisting of hydrogen, alkyl, —SO$_3$Rx, —PO$_3$R$^{y2}$R$^{z2}$, and —C(=O)R;
R$^c$ is selected from the group consisting of —OH and alkyl;
R$^{x2}$, R$^{y2}$ and R$^{z2}$ are each independently selected from the group consisting of hydrogen and a pharmaceutically acceptable cation; and
X is halogen or trifluoromethyl.

In certain embodiments, 2-(4-fluorophenyl)-3-(4-hydroxyphenoxy)benzo[b]thiophen-6-ol (HP-BTF) is excluded as a compound of formula (II).

The estrogen-related medical disorder may be selected from the group consisting of: cancer, inflammation, osteoporosis, vaginal atrophy, central nervous system diseases, and cardiovascular system diseases. The central nervous system diseases may be selected from the group consisting of Alzheimer's Disease and mild cognitive impairment. The cancer may be selected from the group consisting of breast cancer, ovarian cancer, prostate cancer, and lung cancer. The breast cancer may be a tamoxifen resistant breast cancer or a triple negative breast cancer.

The at least one compound of formula (II) may be 3-(4-fluorophenyl)-2-(4-hydroxyphenoxy)benzo[b]thiophen-6-ol or a pharmaceutically acceptable salt thereof.

Also provided herein is a method of identifying a cancer in a subject. The method may comprise obtaining a test sample from the subject having cancer, and determining an amount of PKCα in the test sample. If the amount of PKCα in the test sample is greater than an amount of PKCα in a test sample from a subject not having cancer, then the cancer is sensitive to at least one compound of formula (II)

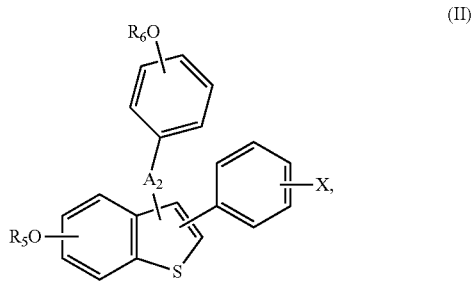

(II)

or a pharmaceutically acceptable salt thereof,
wherein
$A_2$ is —O— or —C(=O)—;
$R_5$ and $R_6$ are each independently selected from the group consisting of hydrogen, alkyl, —SO$_3$R$^{x2}$, —PO$_3$R$^{y2}$R$^{z2}$, and —C(=O)R$^c$;
$R^c$ is selected from the group consisting of —OH and alkyl;
$R^{x2}$, $R^{y2}$ and $R^{z2}$ are each independently selected from the group consisting of hydrogen and a pharmaceutically acceptable cation; and
X is halogen or trifluoromethyl.

In certain embodiments, 2-(4-fluorophenyl)-3-(4-hydroxyphenoxy)benzo[b]thiophen-6-o (HP-BTF) is excluded as a compound of formula (II).

The at least one compound of formula (II) may be 3-(4-fluorophenyl)-2-(4-hydroxyphenoxy)benzo[b]thiophen-6-ol or a pharmaceutically acceptable salt thereof.

In another aspect, disclosed is a compound of formula (I-vii)

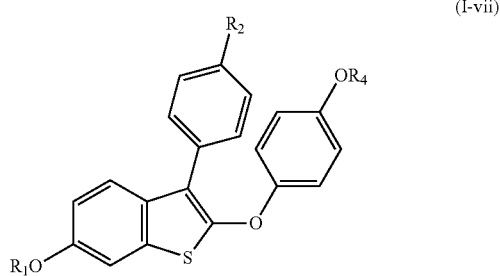

(I-vii)

wherein
$R_1$ is selected from the group consisting of hydrogen, alkyl, —SO$_3$R$^{x1}$, —PO$_3$R$^{y1}$R$^{z1}$, and —C(=O)R$^a$;
$R_2$ is selected from the group consisting of halo and —OR$_3$;
$R_3$ is selected from the group consisting of hydrogen, alkyl, —SO$_3$R$^{x1}$, —PO$_3$R$^{y1}$R$^{z1}$, and —C(=O)R$^a$;

$R_4$ is selected from the group consisting of hydrogen, alkyl, —SO$_3$R$^{x1}$, —PO$_3$R$^{y1}$R$^{z1}$, and —C(=O)R$^a$;
$R^a$, at each occurrence, is independently selected from the group consisting of —OH and alkyl; and
$R^{x1}$, $R^{y1}$ and $R^{z1}$ are, at each occurrence, independently selected from the group consisting of hydrogen and a pharmaceutically acceptable cation.

In certain embodiments, $R_1$ is selected from hydrogen and alkyl (e.g., methyl, ethyl, propyl, butyl). In certain embodiments, $R_1$ is hydrogen. In certain embodiments, $R_1$ is methyl. In certain embodiments, $R_2$ is halo. In certain embodiments, $R_2$ is fluoro. In certain embodiments, $R_4$ is selected from hydrogen and alkyl (e.g., methyl, ethyl, propyl, butyl). In certain embodiments, $R_4$ is hydrogen. In certain embodiments, $R_4$ is methyl. In certain embodiments, $R_1$ is selected from hydrogen and methyl; $R_2$ is fluoro; and $R_4$ is hydrogen.

In certain embodiments, the compound of formula (I-vii) has formula (I-viii)

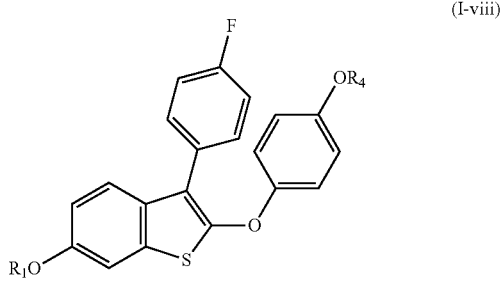

(I-viii)

wherein $R_1$ and $R_4$ are as defined above.

In certain embodiments, the compound of formula (I-vii) has formula (I-ix)

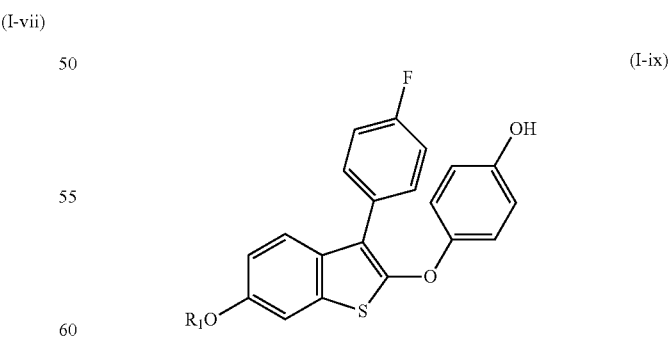

(I-ix)

wherein $R_1$ is as defined above. In certain embodiments, $R_1$ is selected from hydrogen and alkyl (e.g., C$_1$—, C$_2$—, C$_3$—, C$_4$—, C$_5$—, or C$_6$-alkyl).

In certain embodiments, the compound of formula (I-vii) has formula (I-x), also referred to herein as TTC-352,

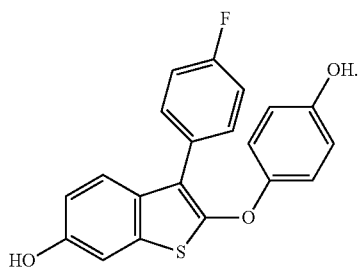

(I-x)

In another aspect, disclosed is a pharmaceutical composition comprising a compound of formula (I-vii), such as TTC-352, and at least one pharmaceutically acceptable carrier.

BRIEF DESCRIPTION OF THE DRAWINGS

FIG. 6A and FIG. 6B show LC-MS/MS MRM chromatograms of BTC and DansylBTC. FIG. 6A) Reconstructed ion chromatogram for the MRM transition of m/z 241→208 of standard BTC (100 ng/mL). FIG. 6B) Reconstructed ion chromatogram for the MRM transition m/z 709→171 of standard DansylBTC (100 ng/mL).

FIG. 7 shows the synthesis of DansylBTC and DansylBR-BTC standards. Reagents and conditions: (a) N-Bromoacetamide, DCM, EtOH, rt; (b) BBn, dry DCM, 0° C.; (c) Dansyl chloride, TEA, DCM, 60° C.

DETAILED DESCRIPTION

Figure 1:
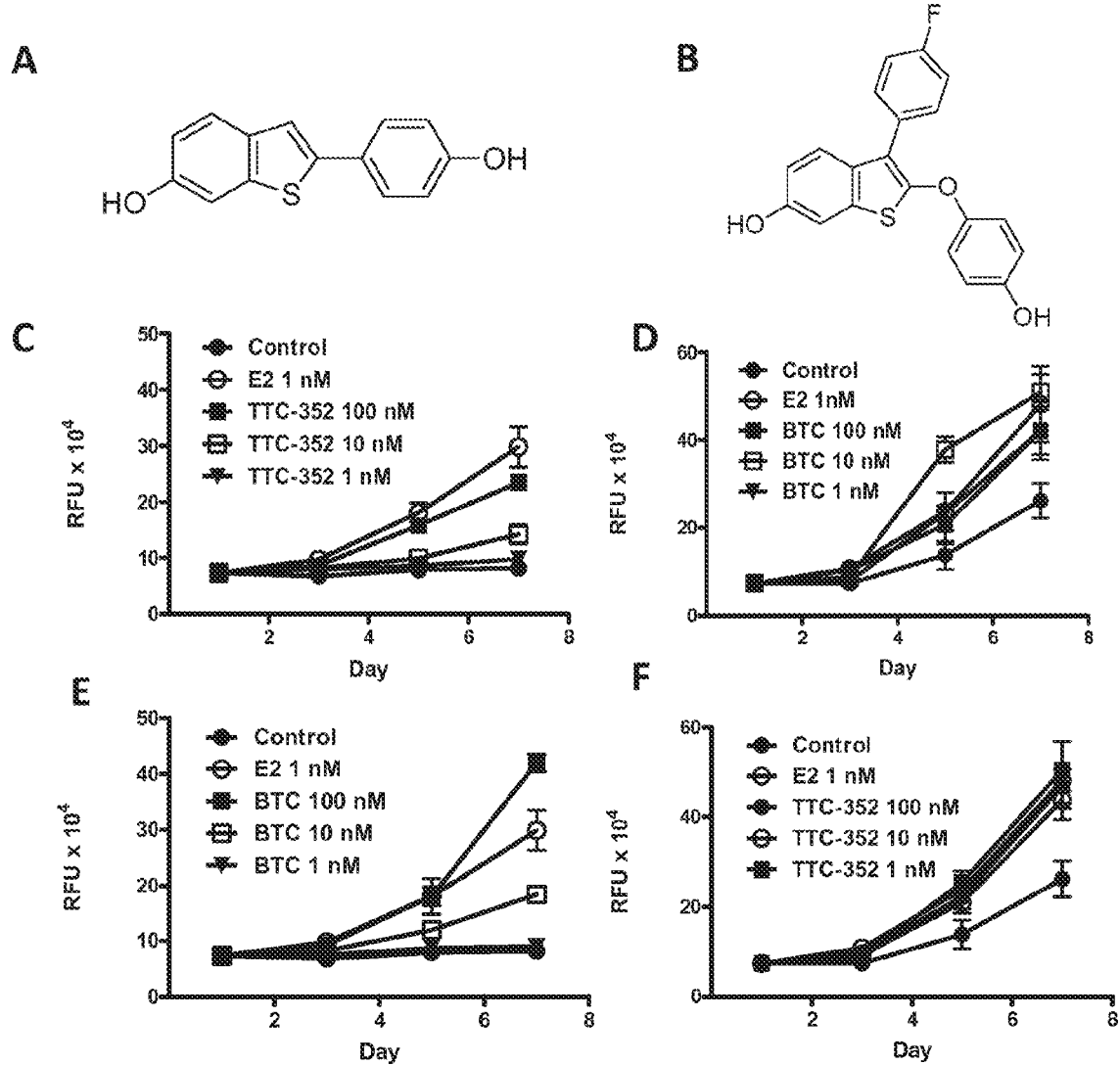
FIG. 1 shows the effect of BTC (i.e., 2-(4-hydroxyphenyl) benzo[b]thiophen-6-ol) and TTC-352 (i.e., 3-(4-fluorophenyl)-2-(4-hydroxyphenoxy)benzo[b]thiophen-6-ol) on the proliferation of T47D:A18/neo and T47D:A18/PKCα cells in vitro. A) Structure of BTC. B) Structure of TTC-352. Effect of BTC treatment on the growth of C) T47D:A18/neo and D) T47D:A18/PKCα cells. Effect of TTC-352 treatment on the growth of E) T47D:A18/neo and F) T47D:A18/PKCα cells. DNA assays were performed as described in Materials and Methods. Graphs show mean SEM and are representative of three independent experiments.

The present invention relates to methods of treatment of estrogen-related medical disorders. An estrogen-related medical disorder may be selected from the group consisting of cancer, inflammation, osteoporosis, vaginal atrophy, central nervous system diseases (e.g., Alzheimer's Disease and mild cognitive impairment), and cardiovascular system diseases. The cancer may be selected from the group consisting of breast cancer, ovarian cancer, prostate cancer, and lung cancer. The breast cancer may be a tamoxifen resistant breast cancer or a triple negative breast cancer.

The methods of treatment may include administering to a subject in need of such treatment a composition comprising a therapeutically effective amount of at least one compound of formula (I) and/or formula (II).

A compound of formula (I) may be

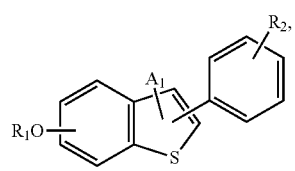

(I)

or a pharmaceutically acceptable salt thereof,
wherein
R$_1$ is selected from the group consisting of hydrogen, alkyl, —SO$_3$R$^{x1}$, —PO$_3$R$^{y1}$R$^{z1}$, and —C(═O)R$^a$;

$R_2$ is selected from the group consisting of halo and —$OR_3$;

$R_3$ is selected from the group consisting of hydrogen, alkyl, —$SO_3R^{x1}$, —$PO_3R^{y1}R^{z1}$, and —$C(=O)R^a$;

$A_1$ is H, alkyl, —$R^{b1}$, —$OR^{b2}$, or —$C(=O)R^{b3}$;

$R^{b1}$, $R^{b2}$, and $R^{b3}$ are each independently selected from the group consisting of is alkyl, cycloalkyl, and phenyl substituted with 1, 2, or 3 substituents independently selected from halo and —$OR_4$;

$R_4$ is selected from the group consisting of hydrogen, alkyl, —$SO_3R^{x1}$, —$PO_3R^{y1}R^{z1}$, and —$C(=O)R^a$;

$R^a$, at each occurrence, is independently selected from the group consisting of —OH and alkyl; and $R^{x1}$, $R^{y1}$ and $R^{z1}$ are, at each occurrence, independently selected from the group consisting of hydrogen and a pharmaceutically acceptable cation;

provided that the compound of formula (I) contains at least one group selected from —$OR_3$ and —$OR_4$.

A compound of formula (II) may be

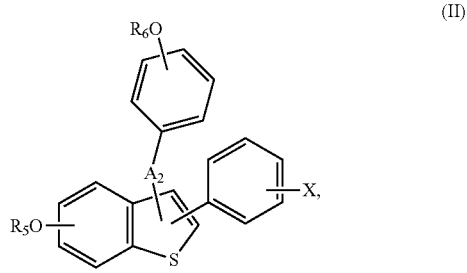

(II)

or a pharmaceutically acceptable salt thereof,
wherein
$A_2$ is —O— or —C(=O)—;

$R^5$ and $R_6$ are each independently selected from the group consisting of hydrogen, alkyl, —$SO_3R^{x2}$, —$PO_3R^{y2}R^{z2}$, and —$C(=O)R^c$;

$R^c$ is selected from the group consisting of —OH and alkyl;

$R^{x2}$, $R^{y2}$ and $R^{z2}$ are each independently selected from the group consisting of hydrogen and a pharmaceutically acceptable cation; and X is halogen or trifluoromethyl.

The at least one compound of formula (I) may also be 2-(4-hydroxyphenyl)benzo[b]thiophen-6-ol, or a pharmaceutically acceptable salt thereof. The at least one compound of formula (II) may also be 3-(4-fluorophenyl)-2-(4-hydroxyphenoxy)benzo[b]thiophen-6-ol or a pharmaceutically acceptable salt thereof. Any combination of the above compounds may also be used in the methods of treatment.

The present invention also relates to methods of identifying a cancer in a subject. The methods may include obtaining a test sample from the subject having cancer and determining an amount of PKCα in the test sample. If the amount of PKCα in the test sample is greater than an amount of PKCα in a test sample from a subject not having cancer, then the cancer may be sensitive to at least one compound of formula (I) and/or formula (II). Additionally, the cancer may be sensitive to pharmaceutically acceptable salts of formula (I) and/or formula (II). The at least one compound of formula (I) may also be 2-(4-hydroxyphenyl)benzo[b]thiophen-6-ol, or a pharmaceutically acceptable salt thereof. The at least one compound of formula (II) may also be 3-(4-fluorophenyl)-2-(4-hydroxyphenoxy)benzo[b]thiophen-6-ol or a pharmaceutically acceptable salt thereof. The cancer may also be sensitive to any combination of the above compounds.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "alkyl" as used herein, refers to a linear or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, pentyl, hexyl, heptyl, octyl, nonyl and decyl.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl. The cycloalkyl groups of this invention may be optionally substituted with 1, 2 or 3 alkyl substituents.

The term "halogen" as used herein, means Cl, Br, I, or F.

The term "pharmaceutically acceptable cation" refers to a positively charged molecule or atom that is balanced by a negatively charged molecule or atom. Representative pharmaceutically acceptable cations include metal salts such as, for example, aluminum, calcium, copper, ferric, ferrous, lithium, magnesium, manganic salts, manganous, potassium, sodium, zinc, and the like as well as nontoxic ammonium, quaternary ammonium and amine cations including, but not limited to ammonium, tetramethylammonium, tetraethylammonium, methylamine, dimethylamine, trimethylamine, triethylamine, ethylamine, naturally occurring substituted amine, cyclic amines, arginine, betnine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, procaine, purines, theobromine, tripropylamine, tromethamine, triethanolamine and the like.

The term "trifluoromethyl" as used herein, means a —$CF_3$ group.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS OF THE INVENTION

Compounds of the invention (also referred to herein as "agents") include compounds of formula I

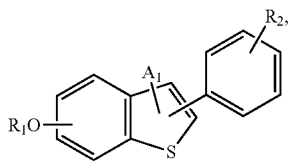
(I)

or a pharmaceutically acceptable salt thereof,
wherein
$R_1$ is selected from the group consisting of hydrogen, alkyl, —SO$_3$R$^1$, —PO$_3$R$^{y1}$R$^{z1}$, and —C(=O)R$^a$;
$R_2$ is selected from the group consisting of halo and —OR$_3$;
$R_3$ is selected from the group consisting of hydrogen, alkyl, —SO$_3$R$^{x1}$, —PO$_3$R$^{y1}$R$^{z1}$, and —C(=O)R$^a$;
$A_1$ is H, alkyl, —R$^{b1}$, —OR$^{b2}$, or —C(=O)R$^{b3}$;
$R^{b1}$, $R^{b2}$, and $R^{b3}$ are each independently selected from the group consisting of is alkyl, cycloalkyl, and phenyl substituted with 1, 2, or 3 substituents independently selected from halo and —OR$_4$;
$R_4$ is selected from the group consisting of hydrogen, alkyl, —SO$_3$R$^{x1}$, —PO$_3$R$^{y1}$R$^{z1}$, and —C(=O)R$^a$;
$R^a$, at each occurrence, is independently selected from the group consisting of —OH and alkyl; and
$R^{x1}$, $R^{y1}$ and $R^{z1}$ are, at each occurrence, independently selected from the group consisting of hydrogen and a pharmaceutically acceptable cation;
provided that the compound of formula (I) contains at least one group selected from —OR$_3$ and —OR$_4$.

Compounds of the invention (also referred to herein as "agents") include compounds of formula(II)

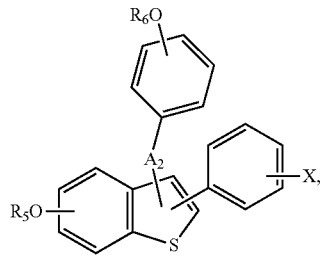
(II)

or a pharmaceutically acceptable salt thereof,
wherein
$A_2$ is —O— or —C(=O)—;
$R_5$ and $R_6$ are each independently selected from the group consisting of hydrogen, alkyl, —SO$_3$R$^{x2}$, —PO$_3$R$^{y2}$R$^{z2}$, and —C(=O)R$^c$;
$R^c$ is selected from the group consisting of —OH and alkyl;
$R^{x2}$, $R^{y2}$ and $R^{z2}$ are each independently selected from the group consisting of hydrogen and a pharmaceutically acceptable cation; and
X is halogen or trifluoromethyl.

a. Compounds of Formula (I)

A compound of formula (I) may be an agonist, an antagonist, a selective estrogen receptor modulator (SERM), or a selective estrogen mimic (SEM). A compound of formula (I) may include 2-(4-hydroxyphenyl)benzo[b]thiophen-6-ol. 2-(4-hydroxyphenyl)benzo[b]thiophen-6-ol may also be known as BTC. The chemical structure of BTC is shown in FIG. 1A.

The compounds of formula (I) may exist as a pharmaceutically acceptable salt. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like, are contemplated as being within the scope of the present invention.

b. Compounds of Formula (II)

A compound of formula (II) may be an agonist, an antagonist, a selective estrogen receptor modulator (SERM), or a selective estrogen mimic (SEM). A compound of formula (II) may include 3-(4-fluorophenyl)-2-(4-hydroxyphenoxy)benzo[b]thiophen-6-ol. 3-(4-fluorophenyl)-2-(4-hydroxyphenoxy)benzo[b]thiophen-6-ol may also be known as TTC-352 or TTC-352. The chemical structure of TTC-352 is shown in FIG. 1B. A compound of formula (II) may include 4-((3-(4-fluorophenyl)-6-methoxybenzo[b]thiophen-2-yl)oxy)phenol. 4-((3-(4-fluorophenyl)-6-methoxybenzo[b]thiophen-2-yl)oxy)phenol may also be known as Monomethoxyl-TTC-352.

The compounds of formula (II) may exist as a pharmaceutically acceptable salt. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenyl-propionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like, are contemplated as being within the scope of the present invention.

3. PHARMACEUTICAL COMPOSITIONS

Compounds of the invention may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of the agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I) may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

In another example, a therapeutically effective amount of a compound of formula (II) may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

4. METHODS OF TREATMENT

The compounds and compositions of the present invention may be used in methods for treatment of estrogen-related medical disorders. The methods of treatment may comprise administering to a subject in need of such treatment a composition comprising a therapeutically effective amount of an agent. The agent may be at least one compound of formula (I). The compound of formula (I) may be BTC. The agent may be at least one compound of formula (II). The compound of formula (II) may be TTC-352.

a. Estrogen-Related Disorders

The compounds and compositions of the present invention may be used in methods for treatment of estrogen-related medical disorders. An estrogen-related medical disorder may be any medical disorder in which the activity of an estrogen receptor is altered or changed. Alteration of the activity of an estrogen receptor may include upregulation or downregulation of estrogen receptor activity. Alteration of the activity of an estrogen receptor may be the same or different in organs, tissues, and/or cells of a subject.

An estrogen-related medical disorder may also be any medical disorder responsive to modulation of the activity of an estrogen receptor. Such modulation of the activity of an estrogen receptor may include upregulation or downregulation of estrogen receptor activity. The activity of an estrogen receptor may be modulated or altered by an agonist, an antagonist, a selective estrogen receptor modulator (SERM), a selective estrogen mimic (SEM), and/or derivatives thereof. The activity of the estrogen receptor may be modulated the same or differently in different organs, tissues, and/or cells of a subject.

An estrogen-related medical disorder may further be any medical disorder caused by the action of estrogen and/or lack of estrogen action. An estrogen-related medical disorder may be any medical disorder responsive or sensitive to a composition of the present invention.

An estrogen-related medical disorder may be hormone dependent or hormone independent. An estrogen-related medical disorder may include, but is not limited to, cancer, inflammation, osteoporosis, vaginal atrophy, central nervous system diseases, and cardiovascular diseases.

(1) Cancer

The methods of the present invention may be used in methods for treatment of estrogen-related medical disorders, for example, cancer. The cancer may be a breast cancer, a uterine cancer, an ovarian cancer, a prostate cancer, and a lung cancer. Particularly, the breast cancer may be a tamoxifen resistant breast cancer or a triple negative breast cancer. A triple negative breast cancer may be a cancer that does not express an estrogen receptor, a progesterone receptor, and an epidermal growth factor receptor 2 (HER-2). The expression or over expression of PKCα may be indicative of or associated with breast cancer and/or other cancers. PKCα may be a biomarker or marker of breast cancer and/or other cancers.

The method of treatment may prevent or reduce the risk of cancer in a subject. The method of treatment may cause partial or complete regression of cancer in a subject. The method of treatment may cause partial or complete regression of a hormone independent cancer in a subject. The method of treatment may cause partial or complete regression of a hormone dependent cancer in a subject.

The method of treatment may antagonize estrogen action in the breast. The method of treatment may block or limit the mitogenic activities of estrogen in the breast, reproductive system, and the prostate. The method of treatment may cause partial or complete regression of a tamoxifen resistant cancer or tumor. The method of treatment may cause partial or complete regression of a triple negative breast cancer.

(2) Inflammation

The methods of the present invention may be used in methods for treatment of estrogen-related medical disorders, for example, inflammation. The methods of treatment may prevent or reduce inflammation in a subject in need of such treatment.

(3) Osteoporosis

The methods of the present invention may be used in methods for treatment of estrogen-related medical disorders, for example, osteoporosis. The methods of treatment may prevent or reduce osteoporosis in a subject in need of such treatment. The methods of treatment may prevent or reduce the loss of bone mineral density in a subject. The methods of treatment may reduce or decrease the rate of bone turnover or fractures. The methods of treatment may improve or maintain bone mineral density in a subject. The methods of treatment may reverse osteoporosis in a subject in need of such treatment.

(4) Vaginal Atrophy

The methods of the present invention may be used in methods for treatment of estrogen-related medical disorders, for example, vaginal atrophy. The methods of treatment may prevent or reduce vaginal atrophy in a subject in need of such treatment. The methods of treatment may reverse vaginal atrophy in a subject in need of such treatment.

(5) Cardiovascular System Diseases

The methods of the present invention may be used in methods for treatment of estrogen-related medical disorders, for example, cardiovascular system diseases. The methods of treatment may enhance or maintain the vasodilatory effects of estradiol on the coronary vasculature. The methods of treatment may decrease or lower low-density lipoprotein cholesterol (LDL-C) levels. The methods of treatment may raise high-density lipoprotein cholesterol (HDL-C) levels. The methods of treatment may decrease or reduce the risk of myocardial infarction. The methods of treatment may prevent or reduce the risk of thromobosis. The methods of treatment may prevent or reduce the risk of stroke. The methods of treatment may prevent or reduce the risk of coronary heart disease.

(6) Central Nervous System Diseases

The methods of the present invention may be used in methods for treatment of estrogen-related medical disorders, for example, central nervous system diseases. The disease of the central nervous system may be Alzheimer's Disease or mild cognitive impairment. The methods of treatment may prevent, reduce, or reverse Alzheimer's Disease or mild cognitive impairment in a subject in need of such treatment. The methods of the present invention may reverse cognitive deficits. The methods of the present invention may restore cognition, long term potentiation (LTP), and synaptic function, and/or be neuroprotective. The methods of present invention may promote neuronal survival and/or hippocampal neurogenesis.

b. Modes of Administration

Methods of treatment may include any number of modes of administering the composition of the present invention. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixiers, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

5. METHOD OF IDENTIFICATION

The present invention also relates to methods of identifying a cancer in a subject. The method may include obtaining a test sample from the subject having cancer and determining an amount of PKCα in the test sample. If the amount of PKCα in the test sample is greater than an amount of PKCα in a test a sample from a subject not having cancer, then the cancer is sensitive to at least one compound of formula (I) and/or formula (II). A compound of formula (I) may be BTC. A compound of formula (II) may be TTC-352.

A cancer sensitive to at least one compound of formula (I) and/or formula (II) may overexpress protein kinase C alpha (PKCα) and/or be resistant to tamoxifen. A subject having a cancer sensitive to at least once compound of formula (I) and/or formula (II) may have an amount of PKCα that is greater than a subject not having cancer and/or not having a cancer sensitive to at least one compound of formula (I) and/or formula (II).

The present invention has multiple aspects, illustrated by the following non-limiting examples.

6. EXAMPLES

TAM-resistant T47D:A8/PKCα tumors regress upon treatment with both E2 and the benzothiophene SERM raloxifene (RAL) (11). RAL has a favorable antiestrogenic profile in the uterus and has proven safety over 15 years of clinical use in postmenopausal osteoporosis and breast cancer chemoprevention. In Examples below, the in vivo effects of two novel benzothiophene SERMs, BTC [2-(4-hydroxyphenyl)benzo[b]thiophen-6-ol] (FIG. 1A) and TTC-352 [3-(4-fluorophenyl)-2-(4-hydroxyphenoxy)benzo[b]thiophen-6-ol] (FIG. 1B) that in contrast to RAL were observed to act as estrogen agonists in T47D:A18 as reflected by proliferation and ERE-luciferase reporter assays. Remarkably, both of these SERMs were able to induce regression of TAM-resistant, hormone-independent T47D:A18/PKCα xenograft tumors in vivo, but neither compound was able to support the growth of hormone-dependent, TAM-sensitive T47D:A18/neo tumors. Importantly, neither SERM caused any significant increase in the uterine weights of these mice. These data indicate that benzothiophene SERMs can be designed for the treatment of endocrine resistant breast cancers as they are estrogenic antitumor agents in the TAM-resistant T47D:A18/PKCα breast cancer model, are devoid of significant estrogenic action in the uterus, and are unable to support the growth of estrogen-sensitive T47D:A18 breast cancer xenografts.

Example 1

Materials and Methods for Examples 2-7

Reagents. DMSO, E2 and TAM were obtained from Sigma-Aldrich (St. Louis, Mo. USA). RAL (Evista®, Eli Lilly and Company, Indianapolis, Ind. USA) was purchased from the University of Illinois at Chicago Hospital Pharmacy. Cell culture reagents were obtained from Life Technologies (Carlsbad, Calif. USA). Tissue culture plasticware was purchased from Becton-Dickinson (Franklin Lakes, N.J. USA). The following antibodies were used: rabbit polyclonal ERα (SP1, Lab Vision, Thermo Scientific, Kalamazoo, Mich. USA), mouse monoclonal 0-actin (Sigma, St. Louis, Mo. USA), anti-rabbit Alexa Fluor 488 (Life Technologies, Carlsbad, Calif. USA) and anti-mouse Cy3 (Jackson Immunoresearch Laboratories, West Grove, Pa.).

Cell culture conditions. Stable transfectant cell lines T47D:A18/neo and T47D:A18/PKCα (6) were maintained in RPMI1640 (phenol red) supplemented with 10% fetal bovine serum (FBS) containing G418 (500 µg/ml). Prior to treatment cell lines were cultured in phenol red-free RPMI 1640 supplemented with 10% 3× dextran-coated charcoal treated FBS (E2-depleted media) for 3 days. Cell lines were routinely tested for Mycoplasm contamination (Myco-Alert™ Mycoplasm Detection Kit, Lonza Ltd., Rockland, Me., USA). No authentications of cell lines were preformed by the authors.

Figure 8:
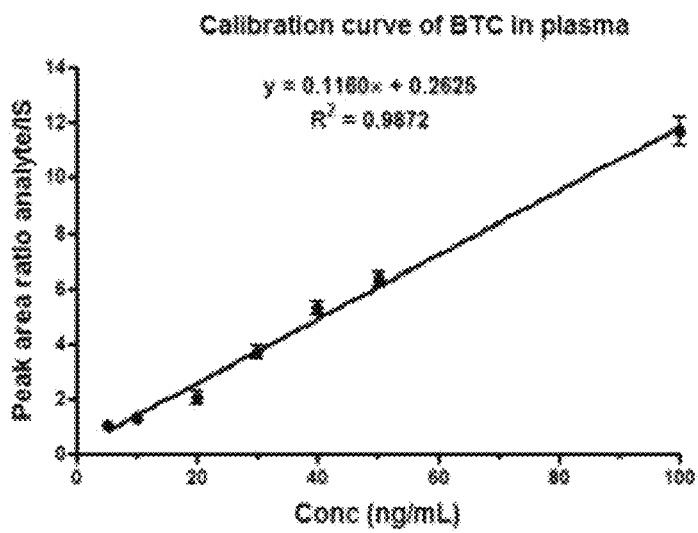
FIG. 8 shows a calibration curve of BTC. The calibration standards were prepared by spiking working solution and IS (20 ng/mL) into blank mouse plasma, giving final BTC plasma concentrations of 5, 10, 20, 30, 40, 50 and 100 ng/mL.

Synthesis and oral bioavailability of benzothiophene SERMs. The synthesis of BTC and HP-BTF has been previously described (12). Dansyl derivatization of BTC was employed to increase limits of detection and quantitation for LC-MS/MS analysis of plasma samples (FIGS. 6 and 7). Working solutions of BTC and internal standard (3-Br-BTC) were prepared by serial dilution of 1 mg/mL acetonitrile stocks. Calibration standards were prepared by spiking BTC or 3-Br-BTC (20 ng/mL) into blank mouse plasma to give a final concentration range of 5-100 ng/mL (FIG. 8). After addition of cold acetonitrile, samples were kept at 4° C. for 2 h, centrifuged at 10,000 rpm for 15 min, and supernatants were concentrated under $N_2$ stream. Resulting residues were reconstituted in 0.1 mL of 100 mM sodium bicarbonate buffer (pH=10.5) and derivatized by addition of 0.1 mL dansyl chloride (2 mg/mL in acetone) followed by incubation at 60° C. for 5 min. After removal of solvent, residues were reconstituted in 0.25 mL acetonitrile/water (1:1, v/v) and analyzed by LC-MS/MS.

BTC was administered in ethanol using a vehicle of propylene glycol/carboxymethylcellulose (10 mg/kg p.o) to ovariectomized 4-6 week old athymic mice (Harlan-Sprague-Dawley) (n=3). Blood samples were collected in EDTA tubes at 20 min, 2 h, and 6 h after treatment. Plasma was separated from whole blood by centrifugation at 4° C. Prior to analysis, plasma was spiked with internal standard and extracted 3× with cold acetonitrile. Recovery of analyte was measured by spiking known amounts of BTC into blank plasma samples. Work up of plasma samples were identical to that described above for standard curve determination.

Figure 9:
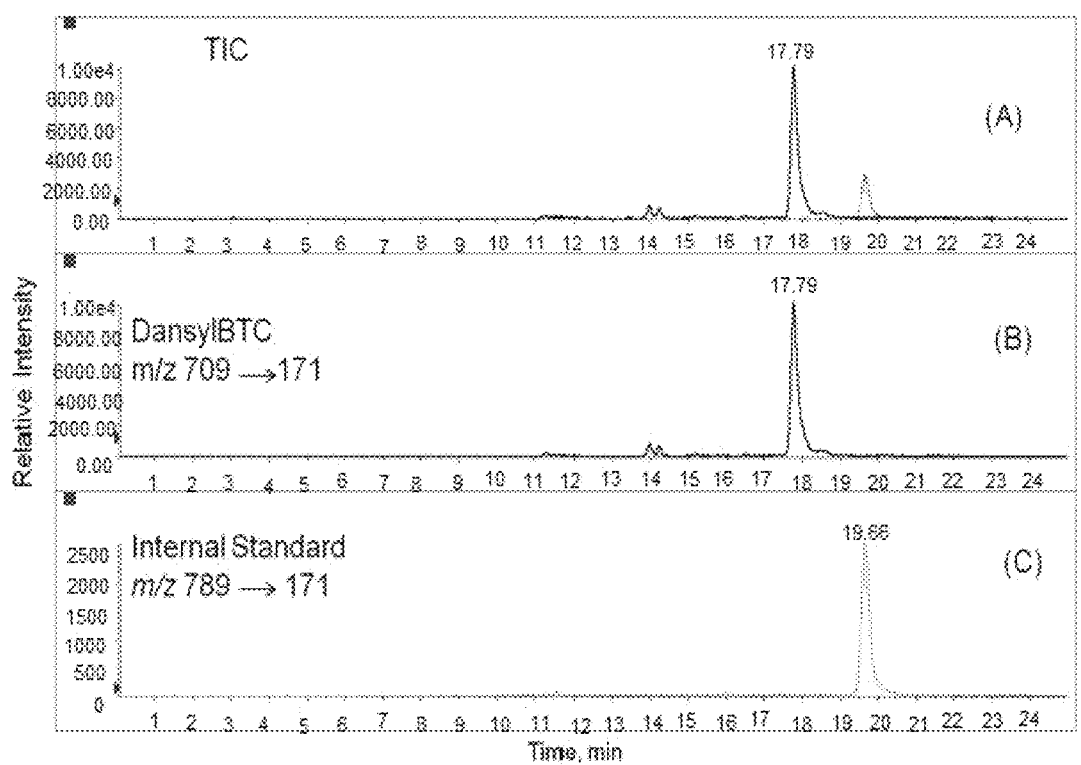
FIG. 9 shows LC-MS/MS MRM chromatograms of DansylBTC and internal standard (DansylBr-BTC). A) Total ion chromatogram. B) BTC (25 g/mL) in mouse plasma. C) IS Br-BTC (20 ng/mL).

LC-MS/MS analysis was performed using an API 3000 (Applied Biosystems) triple quadrupole mass spectrometer equipped with Agilent 1200 HPLC (Agilent Technologies, Santa Clara, Calif. USA). Multiple reaction monitoring (MRM) for the dissociations of m/z 709→171 and m/z 7894171 (loss of 5-dimethylaminonaphthalene) were optimized to measure dansyl-BTC and dansylBr-BTC, respectively (FIG. 9). Separation was performed using a Hypersil BDS C18 (2.1 mm×30 mm; 3 μm) column (Thermo Quest Corporation, MA) at a flow rate of 0.3 mL/min. The elution solvent consisted of water with 10% MeOH and 0.3% formic acid (A) and MeCN with 0.3% formic acid (B). The mobile phase was initially held at 10% B for 5 min, increased to 60% B over 1.5 min, and then increased to 90% B over 15 min, with dansyl-BTC and dansylBr-BTC eluting at 17.8 and 19.7 min, respectively (FIG. 9).

DNA growth assay. T47D:A18/neo and T47D:A18/PKCα cells were maintained in E2-depleted media 3 days before plating in 24-well plates (15,000 cells/well). Medium containing compound was added the following day and total DNA was determined by incubating cells with Hoechst 33342 cell permeable dye and reading fluorescence at excitation 355 nm/emission 460 nm on a Perkin Elmer Victor$^3$ V plate reader (Waltham, Mass. USA). Treatment medium was changed every 2-3 days.

Transient transfection and luciferase assays. Cells were transiently transfected by electroporation with 5 μg ERE-tk-Luc plasmid containing the luciferase reporter gene controlled by a triplet vitellogenin consensus ERE (13) and 1 μgpCMV β-galactosidase (β-gal) expressing plasmid. After 24 hours the cells were treated and incubated overnight at 37° C. Cells were lysed and luciferase activity and β-gal signals were read by a Monolight 3010 luminometer (Becton Dickinson, Franklin Lakes, N.J. USA).

Colony formation assay in MATRIGEL Matrix. MATRIGEL (Becton Dickinson, Franklin Lakes, N.J. USA) was thawed overnight at 4° C. Twelve-well plates were coated with 200 μL MATRIGEL/well and incubated at 37° C. for 30 min. Cells were suspended at 5×103 in 400 μL of phenol red-free RPMI 1640 and spread onto pre-gelled MATRIGEL and allowed to incubate at 37° C. for 30 minutes, and 360 μL of treatment media containing 40 μL MATRIGEL was then added. Plates were incubated at 37° C. for 10 days; medium containing 10% MATRIGEL was replaced to the top of the MATRIGEL every 3 days. Colonies were stained with crystal violet on day 10 and each well was counted by light microscopy (20×).

Growth of T47D:A18/PKCα and T47D:A18/neo tumors in viv. T47D:A18/PKCα and T47D:A18/neo tumors were established as previously described (7). E2 was administered via silastic capsules (1.0 cm) implanted subcutaneously between the scapulae, producing a mean serum E2 level of 379.5 pg/mL (14). BTC and TTC-352 were administered p.o. at a dose of 1.5 mg/animal daily for 2 weeks as previously described for other SERMs (7). RAL was administered p.o. at a dose 1.5 mg/animal daily for 2 weeks. Tumor cross-sectional area was determined weekly using Vernier calipers and calculated using the formula: length/2×width/2×π. Mean tumor area was plotted against time in weeks to monitor tumor growth. The mice were sacrificed by CO2 inhalation and cervical dislocation, and tumors and uteri were excised, cleaned of connective tissue, and immediately weighed. The Animal Care and Use Committee of the University of Illinois at Chicago approved all of the procedures involving animals.

Tumor immunofluorescence confocal microscopy and co-localization analysis. Tumor sections (4 μm) were cut from paraffin blocks and prepared for IF staining by deparaffinization and rehydration. Antigen retrieval was performed by incubating slides in Tris-EDTA (pH=9.0) buffer at 90° C. and allowed to cool at room temperature for 45 min. Slides were blocked with antibody diluent (DAKO, Carpinteria, Calif. USA) for 20 min followed by primary antibody at 1:100 in antibody diluent for 1 h at room temperature. Slides were incubated with fluorescence-conjugated secondary antibodies at 1:100 in antibody diluent for 45 min at room temperature followed by DAPI (4', 6-diamidino-2-phenylindole [1 μg/mL], DAKO, Carpinteria, Calif. USA) for 15 min. Slides were mounted with Vectashield mounting media (Vector Laboratories, Burlingame, Calif. USA). Confocal analysis was performed with a Zeiss LSM 510 microscope (Carl Zeiss, Incorporated, North America, Thornwood, N.Y. USA).

Statistical analyses. Statistics were run using GraphPad Prism Version 5.0. Statistical analyses used were one-way ANOVA followed by Tukey's post-test where appropriate.

Example 2

BTC and TTC-352 Induced T47D:A18/PKCα Growth Inhibition Requires Contact with the Extracellular Matrix We have previously reported that E2 inhibits the growth of T47D:A18/PKCα tumors in vivo and inhibits colony formation in 3D MATRIGEL culture, but has no inhibitory effect in 2D culture. Conversely, the parental empty vector control T47D:A18/neo cell line is growth stimulated by E2 in vitro and in vivo (7, 15). In an effort to find a potential alternative to E2, and to expand on positive data obtained in vivo with RAL (11), two benzothiophene SERMs were selected from a library of SERMs and screened by DNA growth assay in our 2D in vitro model. We have previously reported on examples of this library using: radioligand displacement assays; ERE-luciferase reporter assays in MCF-7 human mammary cancer cells; and alkaline phosphatase activation in Ishikawa human endometrial cancer cells (12, 16-19). In accord with previous data, both BTC and TTC-352 acted as estrogen agonists in T47D:A18/neo and T47D:A18/PKCα cells, stimulating proliferation in 2D cultures. Cells were grown in E2-free media, treated with 0.1% DMSO (vehicle control), E2, BTC or TTC-352 and DNA content was measured as an index of proliferation. T47D:A18/PKCα cells proliferated in the presence of BTC and TTC-352 at all concentrations tested (1 nM, 10 nM, 100 nM) and maximal efficacy was similar to that of E2 (1 nM) observed in vitro (FIGS. 1C and 1E). Interestingly, only the higher concentrations of BTC (100 nM) and TTC-352(100 nM) showed effects on the proliferation of T47D:A18/neo cells comparable to E2(1 nM) treatment (FIGS. 1D and 1F).

Figure 2:
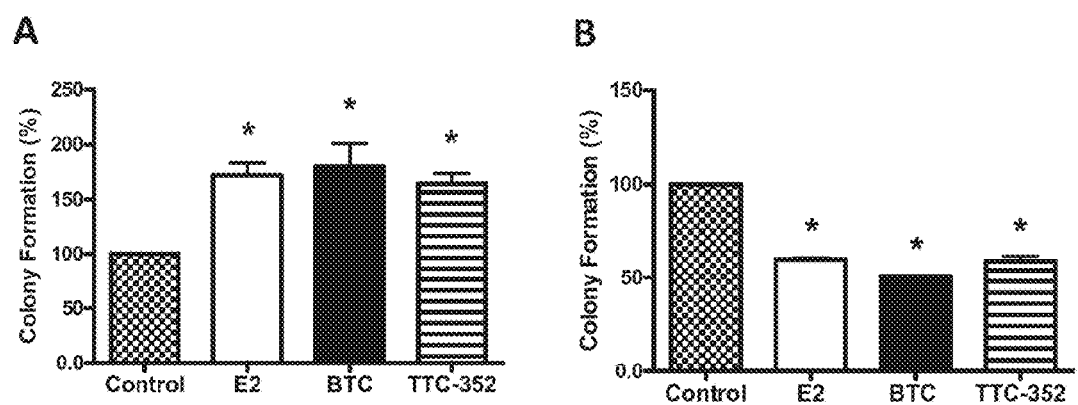
FIG. 2 shows BTC and TTC-352 inhibiting T47D:A18/PKCα colony formation in 3D MATRIGEL. Colonies were established as described in Materials and Methods and treated for 10 days (Control [0.1% DMSO], E2 1 nM, BTC 100 nM, TTC-352 100 nM). *, P<0.05 versus DMSO. Graph shows mean±SEM of 3 independent experiments. A) T47D:A18/neo. B) T47D:A18/PKCα.

E2 inhibits T47D:A18/PKCα colony formation in MATRIGEL (15), in part recapitulating the E2 inhibitory effect on tumor establishment (7). To determine if BTC and TTC-352 similar to E2, can inhibit the growth of T47D: A18/PKCα colonies in 3D culture, colony formation in MATRIGEL was examined. Cells were plated in phenol red-free MATRIGEL containing vehicle (0.1% DMSO), E2 (1 nM), BTC (100 nM), or TTC-352 (100 nM) and allowed to grow for 10 days. These concentrations were selected on the basis of proliferative effects in 2D cultures. T47D:A18/neo colony growth was stimulated by E2, BTC, and TTC-352 treatment (FIG. 2A), while T47D:A18/PKCα colony formation was inhibited in the presence of E2, BTC, and TTC-352 (FIG. 2B). These results indicate that BTC and TTC-352 are estrogenic in vitro and if observations in the 3D culture are predictive of the in vivo outcome, that these SERMs inhibit the growth of T47D:A18/PKCα cells in xenografts.

Example 3

Induction of ERα Transcriptional Activity by BTC and TTC-352 in Breast Cancer Cells RAL is an estrogen antagonist in MCF-7 and Ishikawa cells, whereas TTC-352 is an estrogen agonist, and BTC is an estrogen agonist in MCF-7 and Ishikawa cells. Although BTC and TTC-352 are nanomolar estrogen agonists in Ishikawa cells, it should be noted that potency is three orders of magnitude below that of E2 (16-19). To fully characterize the estrogenic activity of BTC and TTC-352 in T47D:A18/neo and T47D:A18/PKCα cells, we examined transcriptional activation of ERα using an estrogen response element (ERE)-luciferase reporter construct. Following transient co-transfection of the ERE-tk-luc and pCMVD-galactosidase plasmids, cells were treated with vehicle control (0.1% DMSO), E2 (1 nM), BTC (1 nM, 10 nM, 100 nM), or TTC-352(1 nM, 10 nM, 100 nM) 24 hours prior to determining luciferase and β-gal activities. We have previously reported that the basal ERE activity is elevated in T47D: A18/PKCα cells compared to the parental T47D:A18/neo cells (6). In T47D:A18/neo cells, BTC and TTC-352 treatment resulted in an increase in ERα transcriptional activity at the highest concentration of 100 nM (FIG. 3A). T47D: A18/PKCα cells were more sensitive than T47D:A18/neo cells to BTC ERE-luciferase induction at 100 nM and 10 nM (FIG. 3B). These data suggest that BTC and TTC-352 act as ER agonists in both T47D:A18/neo and T47D:A18/PKCα cell lines in vitro, however relative to E2, BTC has enhanced potency and/or efficacy in T47D:A18/PKCα cells.

Example 4

Bioavailability of BTC and Benzothiophene SERMs

Figure 10:
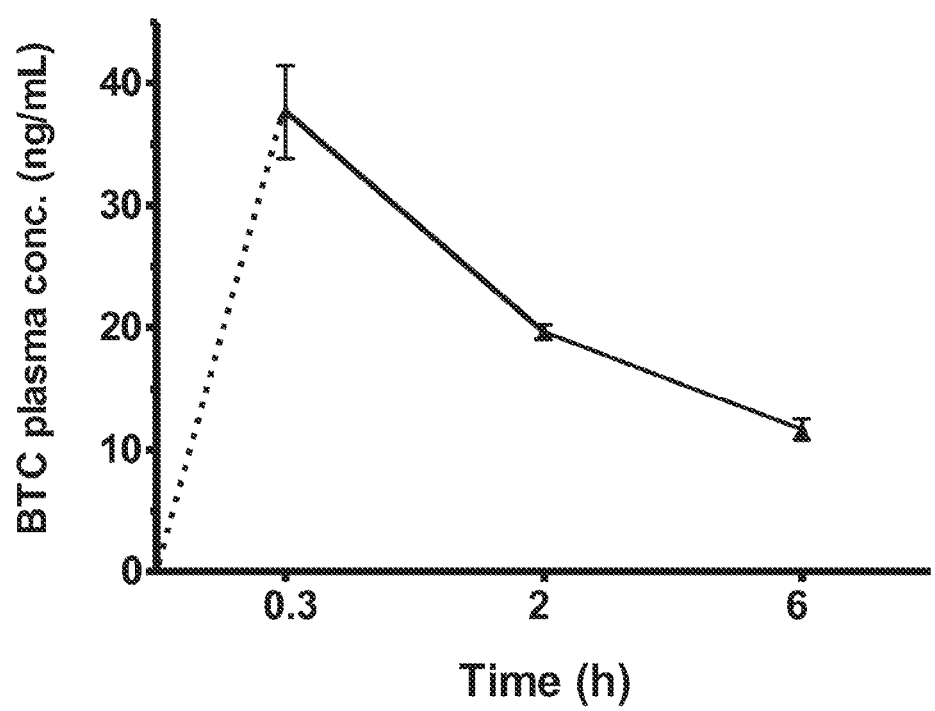
FIG. 10 shows a plasma concentration-time profile of BTC following the administration of a single oral dose of 10 mg/Kg BTC to mice. Each data point represents the mean value SD (n=3).

In humans, the absolute bioavailability of orally administered RAL is reported as 2%, with oral clearance of 441/kg/h (20, 21). Desmethylarzoxifene (DMA) is a more potent estrogen antagonist in the breast and maintains estrogen agonist actions in bone tissues, however, it also has poor bioavailability (22). Arzoxifene was designed as a DMA prodrug to overcome the problems associated with low bioavailability (23-26). As part of a comparative study of biological activity of DMA, arzoxifene and F-DMA in juvenile female rats, metabolism was assessed by quantification of remaining drug in plasma after 3 days of drug administration: DMA was not observed above detection limits (16, 18, 19). BTC is the benzothiophene core of both DMA and RAL, whereas TTC-352 bears structural similarity with F-DMA. Study of the comparative metabolism of DMA and F-DMA suggests that BTC would have low bioavailability on account of metabolism and clearance, in contrast to TTC-352 that is predicted to be stable (18, 19, 26, 27). Therefore, plasma levels of BTC were measured after oral administration to ovariectomized athymic nude mice. Since BTC ionizes poorly by electrosparay ionization ESI-MS, a chemical derivatization method was developed using tandem mass spectroscopic MRM analysis. Drug was detected in plasma at a peak concentration of 40 ng/mL at 30 min, which fell to 10 ng/mL after 6 h (FIG. 10). Given the observation of BTC well above detection limits in mouse plasma, it was decided to compare the effects of BTC and TTC-352 with RAL and E2 in the T47D:A18/PKCα xenograft model using oral delivery.

Example 5

Figure 4:
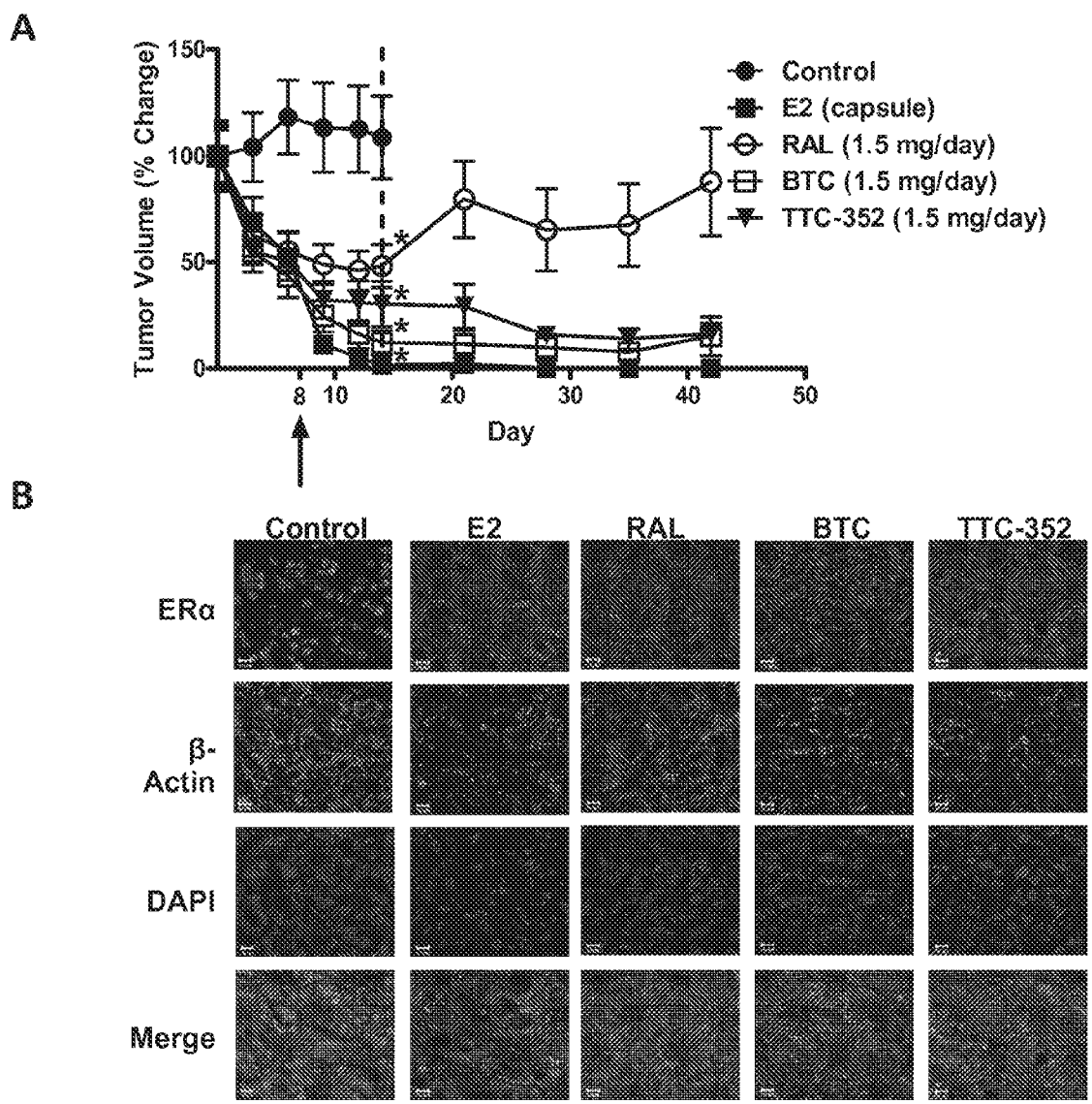
FIG. 4 shows BTC and TTC-352 inhibiting T47D:A18/PKCα xenograft tumors. A) BTC and TTC-352 treatment result in regression of T47D:A18/PKCα tumors. Graph shows percentage of tumor regression (100%-0.5 cm$^2$). Dotted line indicates when treatment was ended. Arrow designates where tumors from (B) were obtained. *, P<0.05 versus control. Graph shows mean t SEM. B) ERα localization in T47D:A18/PKCα tumors by immunofluorescence staining. Total magnification: 630×.

Inhibitory Effect of BTC and TTC-352 Treatment on Hormone-Independent, TAM-Resistant T47D:A18/PKCα Xenografts We have recently reported that RAL treatment results in significant regression of TAM-resistant T47D:A18/PKCα tumors. However, RAL did not produce an effect as robust as E2 on tumor regression and was unable to inhibit MATRIGEL colony formation (11). In contrast to RAL, BTC and TTC-352 are estrogens in 2D culture and like E2 have the ability to inhibit T47D:A18/PKCα colony formation in MATRIGEL (FIG. 2B). Therefore we next examined if these compounds could initiate T47D:A18/PKCα tumor regression. T47D:A18/PKCα cells were injected into 40 athymic mice and were left untreated for seven weeks, at which time the mean tumor size was ~0.5 $cm^2$ (100%/). At seven weeks, the mice were randomized to either continue on the untreated control arm (9 mice), received implants of an E2 capsule (9 mice), oral RAL 1.5 mg/day (9 mice), oral BTC 1.5 mg/day (9 mice), or oral TTC-352 1.5 mg/day (4 mice). Following two weeks, all treatments significantly reduced tumor volume compared to non-treated controls (P<0.05). BTC treated T47D:A18/PKCα tumors regressed by ~88% to a size of ~0.07 $cm^2$ (FIG. 4A) at two weeks. Mice treated with TTC-352 also exhibited a decrease in tumor volume at two weeks regressing by ~70% with a mean tumor volume of ~0.18 $cm^2$ (FIG. 4A). The effect of BTC and HP-BTC was only surpassed by E2 treatment which resulted in ~98% regression at 2 weeks. Both BTC and TTC-352 resulted in a decrease in T47D:A18/PKCα tumor volume that surpassed regression exhibited by RAL (~50%). Furthermore, unlike RAL, regression induced by BTC and TTC-352 was sustained for at least four weeks post-treatment (FIG. 4A).

Regression of T47D:A18/PKCα tumors induced by both RAL and E2 is accompanied by the exit of the estrogen receptor α (ERα) from the nucleus (11). We have previously reported the possible involvement of an extranuclear ER in E2-induced tumor regression (11, 15). Here we show that when tumors treated with BTC and TTC-352 are regressing there is an exit of ERα from the nucleus (FIG. 4B) suggesting that the mechanism underlying regression by benzothiophene SERMs may be similar to that of E2 and RAL and involve extranuclear ERα. Together these results indicate that BTC and TTC-352, like E2, cause T47D:A18/PKCα tumor regression through a mechanism possibly involving extranuclear ERα.

Example 6

Effect of BTC and TTC-352 on Hormone-Dependent T47D:A18/Neo Xenografts

Figure 5:
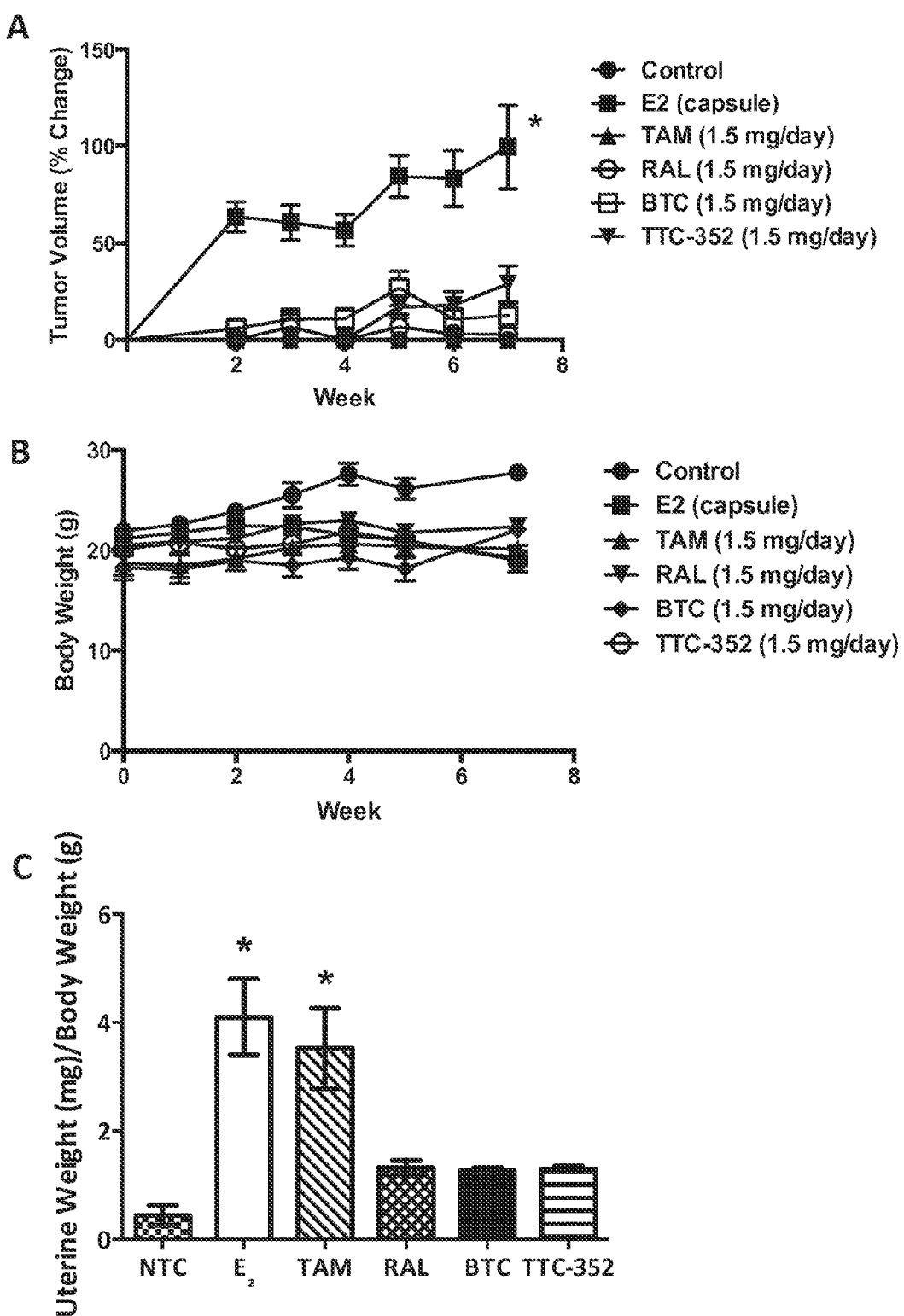
FIG. 5 shows BTC and TTC-352 having no effect on T47D:A18/neo tumor growth, body weight or uterine weights of ovariectomized mice. A) BTC and TTC-352 do not result in growth of T47D:A18/neo tumors. B) Body weights of treated mice from (A). C) Uterine weights from mice in (A). Weights are reported as uterine weight (mg)/body weight (g). *, P<0.05 versus control. Graphs show mean SEM.

The ER positive hormone-dependent T47D:A18/neo empty vector control breast cancer cell line requires E2 for growth in vitro and in vivo (6, 7). Since BTC and TTC-352 treatment result in growth of T47D:A18/neo cells in 2D culture (FIGS. 1C and 1E) and in 3D MATRIGEL (FIG. 2A), we next sought to determine if BTC and TTC-352 could sustain the growth of T47D:A18/neo tumors in vivo. T47D:A18/neo cells were bilaterally injected into the mammary fat pads of 20 athymic mice and divided into six treatment groups (3 non-treated control, 3 E2 capsule, 3 oral TAM 1.5 mg/day, 3 oral RAL 1.5 mg/day, 4 oral BTC 1.5 mg/day, or 4 oral TTC-352 1.5 mg/day). Following seven weeks of treatment, mice treated with E2, as expected, harbored T47D:A18/neo tumors that reached an average size of ~0.35 $cm^2$(100%), tumors treated with BTC and TTC-352, grew to an average size of ~0.04 cm2 and ~0.1 $cm^2$, respectively (FIG. 5A). Although at higher concentrations, BTC and TTC-352 (FIGS. 1C and 1E) stimulated the growth of T47D:A18/neo cells in vitro, neither compound was able to significantly stimulate the growth of T47D:A18/neo xenograft tumors in vivo. Interestingly, the dose capable of causing robust regression of T47D:A18/PKCα tumors had no effect on the growth of T47D:A18/neo tumors in vivo. Additionally, no significant weight loss was observed over the seven week treatment period (FIG. 5B).

Example 7

BTC and TTC-352 have No Effect on Uterine Weights of Athymic Mice

E2 has a proliferative effect on the endometrium resulting in an increase in uterine weight. TAM has an estrogenic effect on endometrial growth, which leads to an increased risk of developing endometrial cancer (28). In ovariectomized rats at a minimally effective dose, RAL did not increase uterine weight in contrast to E2 and TAM, and at doses up to 10 mg/kg/day did not increase luminal epithelial cell thickness (29-32). Mindful of the estrogen agonist actions of BTC and TTC-352 in Ishikawa cells, we sought to compare the effects of BTC and TTC-352 on uterine weight with those of RAL, TAM and E2. Following 7 weeks of treatment the uteri from ovariectomized mice in 5A were excised and weights determined. Interestingly, there was no significant increase in the uterine weights of mice treated with BTC or TTC-352 (FIG. 5C). The significant proliferative actions associated with both TAM and E2 were absent from BTC and TTC-352, indicating that these SERMs deliver an improved safety profile compared to TAM and E2.

Example 8

Summary of Examples 2-7

Resistance to endocrine therapy in breast cancer, whether de novo or acquired, is a major clinical obstacle. The use of 17β-estradiol (E2) or an alternative estrogen has re-emerged as a potential treatment option following exhaustive use of selective estrogen receptor modulators (SERMs), antiestrogens, and aromatase inhibitors. Protein kinase C alpha (PKCα) expression was shown to be a predictor of disease outcome for patients on endocrine therapy and may predict a positive response to an estrogenic treatment. We have previously reported that the ectopic overexpression of PKCα in T47D:A18 breast cancer cells leads to a hormone-independent, tamoxifen (TAM)-resistant, and E2 inhibited phenotype in vivo, recapitulating observations made in the clinic. Here, using our clinically relevant T47D:A18/PKCα model, we have investigated novel benzothiophene SERMs for the treatment of TAM-resistant breast cancer. Treatment with these SERMs resulted in significant regression of T47D:A18/PKCα tumors following two weeks of treatment accompanied by translocation of ERα to extranuclear sites. Importantly, SERM treatment did not result in growth of parental E2-dependent T47D:A18/neo tumors, suggesting that these SERMs do not act as estrogen agonists in parental, hormone-dependent cells in vivo. Additionally, treatment with SERMs did not stimulate uterine weight gain.

Example 9

Discussion of Examples 2-7

Resistance to endocrine therapies is a major obstacle encountered in the clinical setting. Currently there is a lack of effective therapeutic options for women who no longer respond to conventional endocrine therapy approaches. Our findings and those of others suggest that PKCα expression is a predictive marker of disease outcome for patients on endocrine therapy (3-5). Further its expression may predict a positive response to E2 or an E2-like compound (7). E2 has clinical efficacy (9, 10, 33, 34), but due to unfavorable side effects it is no longer used for treatment. In the present study, we sought to identify possible alternative therapeutic options for TAM-resistant breast cancers, especially those overexpressing PKCα.

Figure 3:
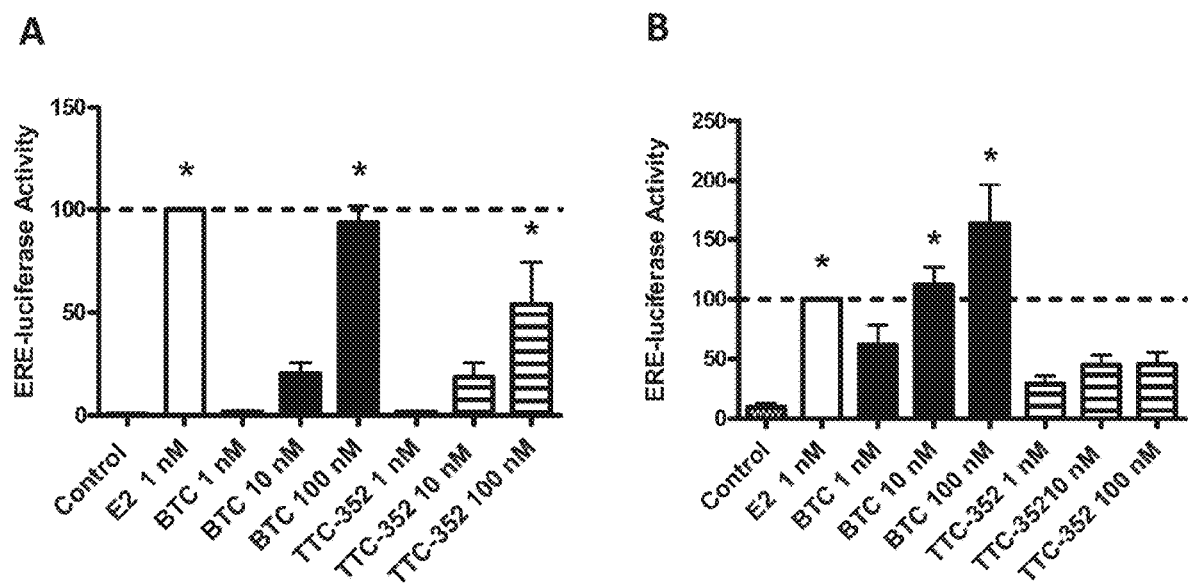
FIG. 3 shows BTC and TTC-352 inducing ERα transcriptional activity in T47D:A18/neo and T47D:A18/PKCα cell lines. A) T47D:A18/neo and B) T47D:A18/PKCα cell lines. Data is expressed normalized to E2 (100%). *, P<0.05 versus DMSO. Graph shows mean SEM of 3 independent experiments.

We screened a number of benzothiophene analogs and based on their in vitro estrogenic activity we chose two analogs, BTC and TTC-352, for further study. In both T47D:A18/neo and T47D:A18/PKCα cells, BTC and TTC-352 treatment led to increased proliferation and activation of ERE in vitro (FIGS. 1 and 3). Although E2 induced the growth of hormone-dependent, TAM-sensitive, parental T47D:A18/neo tumors in vivo, neither BTC nor TTC-352 were able to support T47D:A18/neo tumor growth (FIG. 5A). Interestingly, the TAM-resistant T47D:A18/PKCα tumors that were shown previously to regress upon E2 treatment (7), also regress when treated with BTC or TTC-352 (FIG. 4A). Similar to E2, regression is also accompanied by exit of ERα from the nucleus to extranuclear sites (FIG. 4B) suggesting a potential role for extranuclear ERα in BTC and TTC-352 induced tumor regression. Extranuclear ERα non-genomic responses are generally associated with a proliferative response through activation of various signaling cascades (35-38). We have previously shown that as T47D:A18/PKCα tumors regress in the presence of E2 there is a downregulation of the AKT pathway (15) as well as exit of ERα from the nucleus to extranuclear sites (11), suggesting that extranuclear ERα may have a novel anti-proliferative role in SERM induced T47D:A18/PKCα tumor regression. It is interesting to postulate a mechanism in which extranuclear ERα either directly or indirectly associates with PKCα leading to its inactivation as T47D:A18/PKCα tumors regress. These possibilities are currently being explored in our laboratory. However, unlike E2, neither BTC nor TTC-352 treatment resulted in an increase in the uterine weights of mice (FIG. 5C) indicating that BTC and TTC-352, unlike E2, has enhanced tissue specificity.

Translocation of ERα from the nucleus to cytoplasm is a common feature of treatments that cause regression of T47D:A18/PKCα tumors, but not those that are ineffective, i.e. TAM (11). The similarity with the diarylthiohydantoin antiandrogens (e.g. MDV3100, ARN509, RD162) that cause a similar translocation of the androgen receptor (AR) in prostate cancer cells is of interest, in particular because this feature is seen as a clinical advantage over older antiandrogens (39, 40). MDV3100 is anticipated shortly to receive approval for treatment of castration-resistant prostate cancer. The mechanism by which these antiandrogens cause translocation have not been defined, and as for benzothiophene SERMs could include stabilization of cytoplasmic or destabilization of nuclear receptor complexes.

It is fascinating that structurally related SERMs, variously showing classical ERα antagonist activity (RAL), or classical agonist activity (BTC, TTC-352) should elicit the same tumor regressing actions in T47D:A18/PKCα xenografts, although the failure of RAL-induced regression to persist after drug withdrawal is noted. That the estrogen agonists, BTC and TTC-352, did not stimulate growth of estrogen-sensitive T47D:A18/neo xenografts or uterine tissues is most simply rationalized by the relatively low potency of these agonists, again indicating involvement of a pathway that is not simply classical ERG mediated in T47D:A18/PKCα xenografts.

Recently, the use of E2 or an E2-like compound has re-emerged as a possible treatment strategy for patients exhibiting endocrine therapy resistant breast cancers (41-44). Clinical trials have demonstrated the efficacy of E2 in this setting (33, 34). In fact, a long-term follow up study indicated a survival advantage for patients treated with the synthetic estrogen DES compared to patients treated with TAM (45). The basis for the clinical use of estrogens is supported by a number of preclinical laboratory models (7, 8, 46-52). Shim and colleagues showed that long term E2 deprived MCF-7 cells form tumors that are inhibited by E2 (52). RAL resistant MCF-7 cells undergo apoptosis following E2 exposure (48). The serial transplantation of TAM-stimulated MCF-7 tumors for 5 years also led to an E2 inhibitory phenotype (8) as well as the over-expression of PKCα (7). The ability to predict a patient's response to therapy prior to treatment would be a very attractive clinical option. Patients presenting with tumors overexpressing PKCα would likely benefit from an E2-like therapy, of which there are currently few options.

The results of the present study support the use of a second-line SERM with selective estrogenic effects on the breast for use in patients that no longer respond to conventional endocrine therapy and whose tumors overexpress PKCα. We have described two novel benzothiophene SERMs that cause tumor regression in the TAM-resistant T47D:A18/PKCα model, while having little effect on the growth of parental hormone-dependent T47D:A18/neo tumors. As the presence of PKCα dictated an enhanced estrogenic response to BTC and TTC-352 as well as a tumor regressing phenotype, these compounds have potential clinical value in the TAM-resistant setting. Importantly treatment with BTC and TTC-352 had minimal effects on proliferation within the uteri of mice in vivo indicating that the estrogenic effects of these agents are specific to the breast. Both BTC and TTC-352 are potential alternatives to E2 treatment and represent chemical probes and lead compounds for further optimization towards new treatment options in the management of endocrine resistant breast cancer.

Example 10

Figure 12:
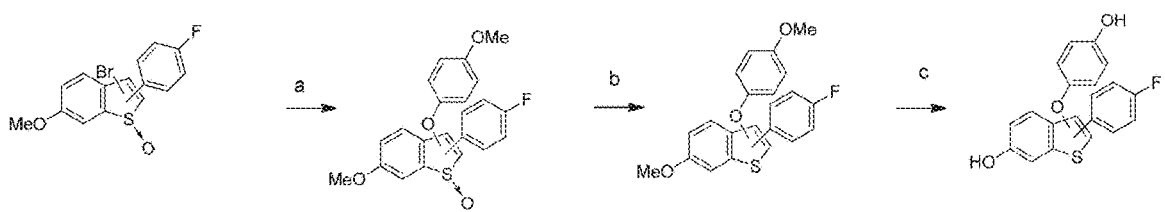
FIG. 12 shows the synthesis of TTC-352 and BM2-153 prodrugs.
Figure 12:
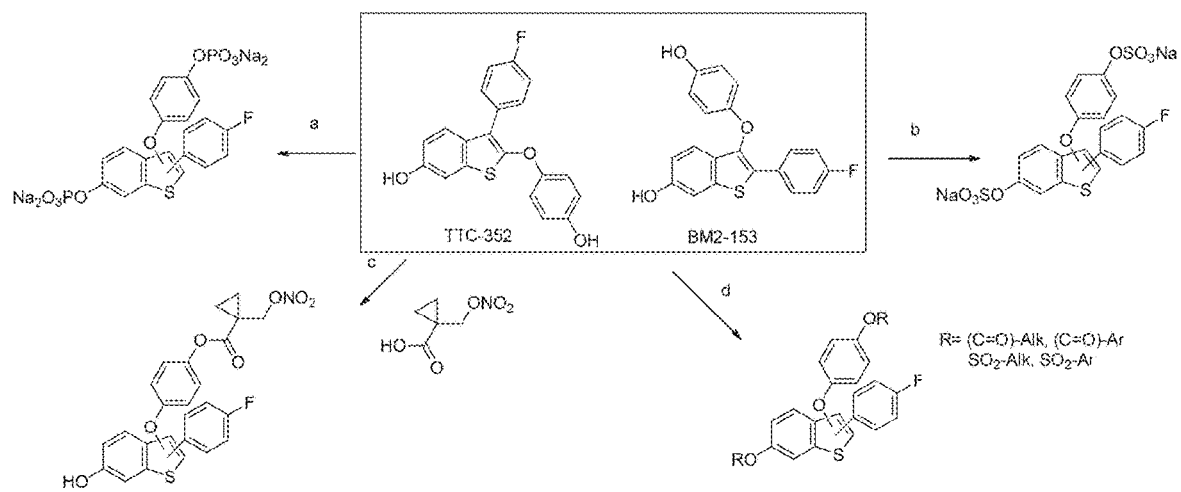

Synthesis of TTC-352 and BM2-153 prodrugs (FIG. 12)

4-((6-acetoxy-2-(4-fluorophenyl)benzo[b]thiophen-3-yl)oxy)phenyl acetate (BM2-153-diacetate). Acetyl chloride (0.312 mmol) was added in one portion to a stirred solution of 2-(4-fluorophenyl)-3-(4-hydroxyphenoxy)benzo[b]thiophen-6-ol (BM2-153, 50 mg, 0.142 mmol) and triethylamine (0.355 mmol) in anhydrous dichloromethane (1 mL) at 0° C. The solution was stirred for 1 h at room temperature and then quenched with $H_2O$ (1 mL). Volatiles were removed in vacuo and the resulting residue was partitioned between $H_2O$ and ethyl acetate. The organic layer was isolated, dried over anhydrous $MgSO_4$, chromatographed onto silica gel, and purified by flash chromatography (hexanes:ethyl acetate, 1:1) to give 61 mg (98%) of the desired compound as a white solid. $^1$HNMR (CDCl$_3$, 400 MHz): δ 7.73 (q, 2H, J=7.2 Hz), 7.57 (d, 1H, J=2 Hz), 7.41 (d, 1H, J=8 Hz), 7.12-6.95 (m, 7H), 2.35 (s, 3H), 2.29 (s, 3H); $^{13}$CNMR (CDCl$_3$, 400 MHz): δ 169.54, 169.48, 154.89, 148.47, 145.57, 139.80, 136.05, 131.54, 129.58, 129.50, 128.91, 122.71, 122.24, 119.29, 116.15, 116.05, 115.83, 115.59, 21.11, 21.03.

2-(4-fluorophenyl)-3-(4-(isobutyryloxy)phenoxy)benzo[b]thiophen-6-yl isobutyrate (BM2-153-diisobutyrate). Isobutyryl chloride (0.312 mmol) was added in one portion to a stirred solution of 2-(4-fluorophenyl)-3-(4-hydroxyphenoxy)benzo[b]thiophen-6-ol (BM21-53, 50 mg, 0.142 mmol) and triethylamine (0.355 mmol) in anhydrous dichloromethane (1 mL) at 0° C. The solution was stirred for 1 h at room temperature and then quenched with $H_2O$ (1 mL). Volatiles were removed in vacuo and the resulting residue was partitioned between $H_2O$ and ethyl acetate. The organic layer was isolated, dried over anhydrous $MgSO_4$, chromatographed onto silica gel, and purified by flash chromatography (hexanes:ethyl acetate, 4:1) to give 56 mg (80%) of the desired compound as a white solid. $^1$HNMR (CDCl$_3$, 400 MHz): δ 7.73 (q, 2H, J=7.2 Hz), 7.57 (d, 1H, J=1.6 Hz), 7.40 (d, 1H, J=8.4 Hz), 7.10-6.94 (m, 7H), 2.89-2.75 (m, 2H), 1.37-1.34 (m, 6H), 1.32-1.29 (m, 6H); $^3$CNMR (CDCl$_3$, 400 MHz): 175.31, 175.25, 154.45, 148.33, 145.38, 139.47, 135.68, 131.05, 129.30, 129.19, 129.11, 128.36, 122.27, 121.81, 118.88, 115.73, 115.65, 115.56, 115.44, 115.16, 33.82, 33.71, 18.54, 18.51.

2-(4-fluorophenyl)-3-(4-(pivaloyloxy)phenoxy)benzo[b]thiophen-6-yl pivalate (BM2-153-dipivalate). Pivaloyl chloride (0.312 mmol) was added in one portion to a stirred solution of 2-(4-fluorophenyl)-3-(4-hydroxyphenoxy)benzo[b]thiophen-6-ol (BM2-153, 50 mg, 0.142 mmol) and triethylamine (0.355 mmol) in anhydrous dichloromethane (1 mL) at 0° C. The solution was stirred for 1 h at room temperature and then quenched with $H_2O$ (1 mL). Volatiles were removed in vacuo and the resulting residue was partitioned between $H_2O$ and ethyl acetate. The organic layer was isolated, dried over anhydrous $MgS_4$, chromatographed onto silica gel, and purified by flash chromatography (hexanes:ethyl acetate, 14:1) to give 65 mg (88%) of the desired compound as a white solid. $^1$HNMR (CDCl$_3$, 400 MHz): 7.73 (q, 2H, J=7.2 Hz), 7.55 (d, 1H, J=1.6 Hz), 7.40 (d, 1H, J=8.8 Hz), 7.08 (t, 2H, J=8.8 Hz), 6.99 (dd, 1H, J=8.8

Hz, 2 Hz), 6.97-6.94 (m, 4H), 1.40 (s, 9H), 1.35 (s, 9H); $^1$CNMR (CDCl$_3$, 400 MHz): δ 177.17, 177.11, 154.79, 148.93, 145.95, 136.05, 131.37, 129.55, 129.47, 128.66, 122.69, 122.61, 122.15, 119.23, 116.08, 116.02, 115.80, 115.52, 39.15, 39.00, 27.22, 27.12, 27.09.

Example 11

TTC-352 (i.e., TTC-352) Treatment Results in Regression of TAM-Resistant Xenograft Tumors without the Side-Effects Associated with Other Treatments In accordance with clinical observations, both T47D-Tam1 and T47D/PKCα xenografts are TAM-resistant and growth is inhibited by E2 treatment (FIG. 11B,C). Interestingly, the newer generation Selective estrogen Receptor Modulator (SERM), raloxifene, caused tumor regression, however, drug withdrawal led to relapse (FIG. 11C). Observations that TTC-352 (FIG. 11A), structurally related to raloxifene, mimicked the actions of E2 in T47D cells in vitro, endorsed TTC-352 as a potential alternative treatment to E2. Established T47D-Tam1 (FIG. 11B) and T47D/PKCα (FIG. 11C) xenograft tumors treated daily with TTC-352 for seven weeks displayed tumor regression comparable to that of E2-treated tumors, even after withdrawal of treatment (FIG. 11C). Endometrial thickening, caused by both E$_2$ and TAM, but not raloxifene, is directly associated with gynecological carcinogenesis and uterine cancer. TTC-352 treatment did not increase uterine weight in mice suggesting negligible hormonal stimulation in gynecological tissues (FIG. 11D). TTC-352 meets the criteria for a selective estrogen mimic (SEM), selective for therapy of ER+ and TAM-resistant breast cancer, with enhanced safety compared to E2 and TAM. PKCα is present in 70% of all tumors, including triple-negative BC, for which there is no effective treatment, indicating the effectiveness of SEM therapeutic application beyond TAM-resistance.

Example 12

Pharmacokinetics of SEMs in Mice

SEM prodrugs have been prepared using standard, scalable organic chemistry techniques. Metabolic stability will be verified in human liver and human intestinal microsomal incubations, and plasma, with or without esterase (PLE). SEMs with high stability, minimal oxidative metabolites, and efficient enzymic bioactivation to TTC-352 (i.e., TTC-352) will be advanced to pharmacokinetic studies.

Ovariectomized (OVX) nude 4-to 6-week-old athymic mice will be administered TTC-352 and no more than 3 SEM prodrugs by gavage in ethanol using a vehicle of propylene glycol/carboxymethyl cellulose at a single dose of 4.4 µmol (equivalent to 1.5 mg/day used in xenograft studies). Blood samples will be collected at 20 min, 2 h, and 6 h after treatment, using EDTA as an anticoagulant. Plasma will be separated from whole blood by centrifugation at 4° C. and samples will be immediately analyzed for prodrug and drug using LC-MS/MS.

Example 13

Figure 11:
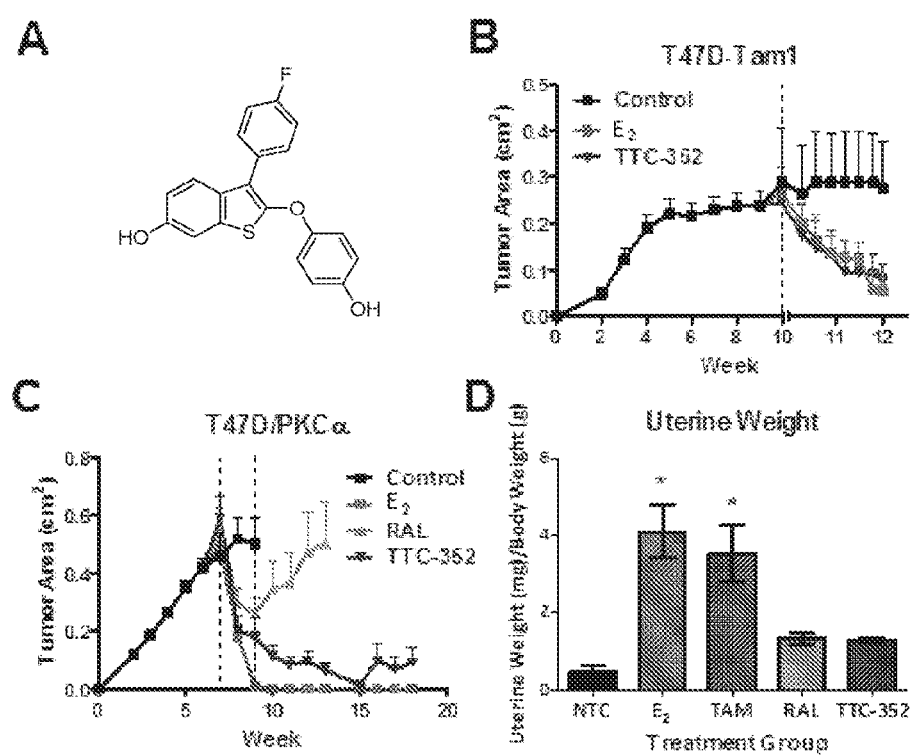
FIG. 11 shows that TTC-352(i.e., TTC-352) treatment results in regression of TAM-resistant xenograft tumors without the side-effects associated with other treatments. A) Structure of TTC-352. B) T47D/Tam1 and C) T47D/PKCα tumors treated with 1.5 mg/day TTC-352 p.o.The SERM raloxifene (1.5 mg/day) was included in T47D/PKCα study. Dotted line represents start of treatment. D) Uterine weights of mice treated with E2 (1 cm capsule), TAM (1.5 mg/day), raloxifene (1.5 mg/day) and TTC-352 (1.5 mg/day). E2 and TAM served as positive controls. Raloxifene served as a negative control. * P<0.05.

Efficacy of TTC-352 (i.e., TTC-352 Prodrugs) on TAM-Resistant Zenograft Tumor Growth T47D-Tam1 and T47D/PKCα xenograft tumor models will be used to assess the efficacy of 2 SEM treatments at 2 doses (4.4 µmol and 0.44 µmol/day, based upon data shown in FIG. 11). Tumors will be grown in OVX athymic mice and treated once tumor volume reaches approximately 0.5 cm$^2$. The response to SEMs will be compared to the standard of care (e.g., tamoxifen).

Example 14

Mechanism of Action Confirmation

For tumors treated by SEMs, PKCα, and ER biomarkers will be assessed by immunohistochemistry. Anticoagulant activity will be measured ex vivo.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

Example 15

Figure 13:
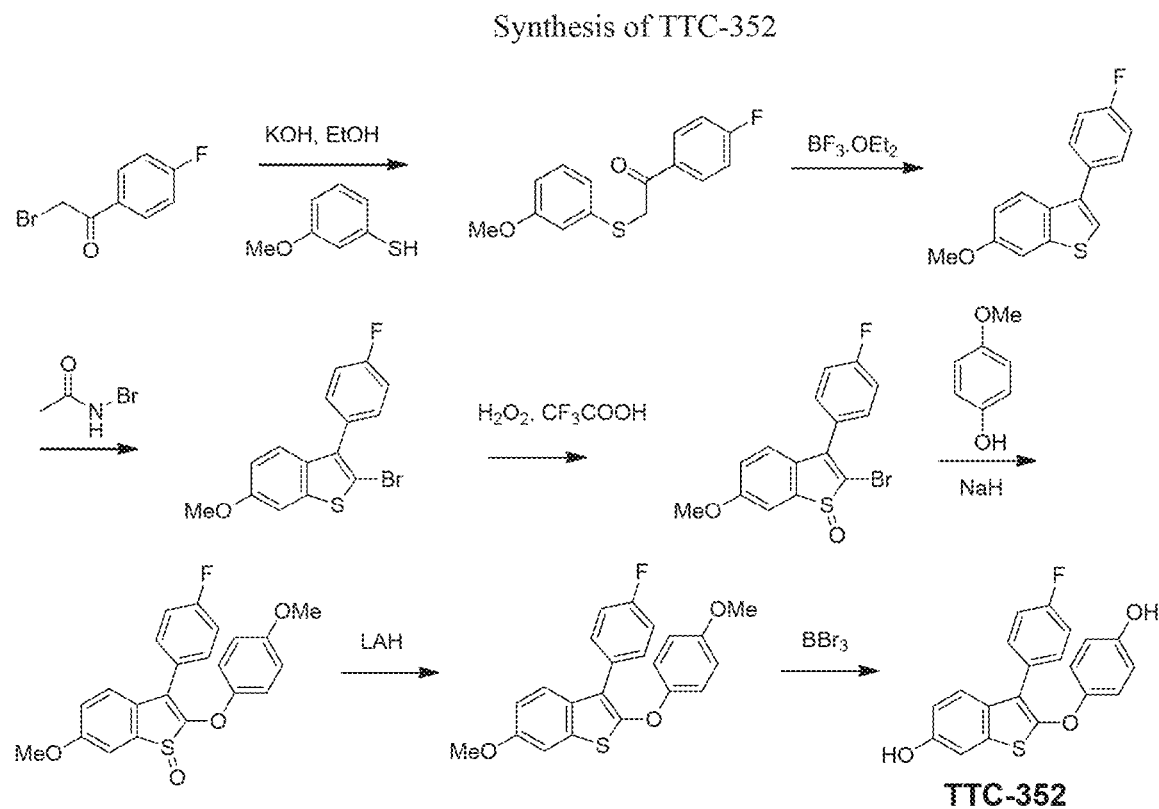
FIG. 13 shows the synthesis of TTC-352.

Synthesis of TTC-352 (FIG. 13)

The compound 3-(4-fluorophenyl)-2-(4-hydroxyphenoxy)benzo[b]thiophen-6-ol (TTC-352) can be prepared according to the scheme above and the following examples.

1-(4-Fluorophenyl)-2-(3-methoxyphenylsulfanyl)ethanone. 3-Methoxybenzenethiol (1 g, 7.1 mmol) was added in one portion to a freshly prepared solution of 7.5 mL of ethanol, 3 mL of water, and 470 mg of KOH (8.4 mmol). The solution was cooled to 5-10° C. A solution of 2-bromo-1-(4-fluorophenyl)ethanone (1.54 g, 7.1 mmol) in 2.5 mLofEtOAc was added to this solution at a rate such that the temperature did not exceed 25° C., and the reaction mixture was allowed to stir overnight at room temperature. The solvents were removed under reduced pressure, and the residue was partitioned between water and ethyl acetate. The aqueous layer was isolated and extracted several times with ethyl acetate, and the combined extracts were washed with consecutive portions of 10% HCl, water, saturated NaHCO$_3$, and water before being dried over anhydrous Na2SO4. After concentration in vacuo to an oil, the crude product was purified by flash chromatography[SiO$_2$, hexane/ethyl acetate (10:1, v/v)] to give 1.4 g (74%) desired product. 1H NMR (300 MHz, DMSO-d) 63.73 (s, 3H), 4.67 (s, 3H), 6.75 (m, 1H), 6.91 (m, 2H), 7.18 (t, J) 8.2 Hz, 1H), 7.34 (t, J) 8.9 Hz, 2H), 8.12 (q, J) 8.9 Hz, 2H).

3-(4-fluorophenyl)-6-methoxybenzo[b]thiophene. A flask was charged with 1-(4-Fluorophenyl)-2-(3-methoxyphenylsulfanyl)ethanone and BF$_3$.OEt$_2$ under Argon atmosphere at room temperature. The reaction mixture was stirred until starting material was consumed as monitored by TLC. The reaction mixture was pured into saturated NaHCO$_3$/ice water, stirred 30 min, and extracted with dichloromethane. The crude product was purified by flash chromatography [SiO$_2$, hexane/dichloromethane (20:1, v/v)]. The combined fractions from column was recrystalized to get 50% pure product. $^1$H NMR (400 MHz, CDCl$_3$) (ppm) 3.89 (s, 3H), 7.02 (dd, 8.9 Hz, 2.2 Hz 1H), 7.15 (m, 3H), 7.37 (d, 2.2 Hz1H), 7.52 (m, 2H), 7.71 (d, 8.9 Hz, 1H), DC NMR (100 MHz, CDCl₃) δ (ppm) 55.62, 105.24, 114.52, 115.50, 115.71, 120.67, 123.30, 130.09, 130.17, 131.96, 132.17, 136.62, 142.07, 157.56, 162.31.

2-bromo-3-(4-fluorophenyl)-6-metboxybenzo[b]thiophene. N-Bromoacetamide (1.46 g, 10.5 mmol) in 10 mL of ethanol was added dropwise to a solution of 3-(4-fluorophenyl)-6-methoxybenzo[b]thiophene(2.58 g, 10 mmol) in 300 mL of CH₂Cl₂ and 20 mL of ethanol at room temperature. After the mixture was stirred for 1 h, the solvent was removed in vacuo. Next, the residue was titrated with ethanol and filtered to give 3.0 g (89%) of desired product. ¹H NMR (400 MHz, CDCl₃) δ (ppm) 3.898 (s, 3H), 6.94 (dd, 8.9 Hz, 2.3 Hz 1H), 7.24 (m, 3H), 7.38 (d, 8.9 Hz1H), 7.45 (m, 2H)), ¹³C NMR (100 MHz, CDCl₃) (ppm) 55.27, 104.1, 109.47, 114.20, 115.14, 115.36, 122.99, 129.57, 131.23, 131.31, 132.29, 135.28, 140.61, 157.36, 162.05.

2-bromo-3-(4-fluorophenyl)-6-methoxybenzo[b]thiophene 1-oxide. Trifluoacetic acid (13 mL) was added dropwise to a solution of 2-bromo-3-(4-fluorophenyl)-6-methoxybenzo[b]thiophene(2.4 g, 7 mmol) in 13 mL of anhydrous CH₂Cl₂. After the mixture was stirred for 5 min, H₂O₂ (1.0 mL, 7 mmol, 30% aqueous solution) was added dropwise, and the resulting mixture was stirred for 2 h at room temperature. Sodium bisulfite (0.3 g) was added to the solution followed by 5 mL of water. The mixture was stirred vigorously for 30 min and then concentrated in vacuo. The residue was partitioned between CH₂Cl₂ and saturated aqueous NaHCO₃ solution(50 mL each). The layers were separated, and the organic layer was washed with consecutive portions of water, saturated NaHCO₃, and water, and then dried over anhydrous Na₂SO₄ and concentrated in vacuo; the residue was titrated with diethylether and filtered to give 2.1 g (84%) of desired product.

3-(4-fluorophenyl)-6-methoxy-2-(4-methoxyphenoxy)benzo[b]thiophene 1-oxide. NaH (237 mg, 9.9 mmol, 60% dispersion in mineral oil) was added to a solution of 4-methoxyphenol (1.31 g, 59 mmol) in 25 mL of anhydrous DMF at room temperature. After the mixture was stirred for 15 min, 2-bromo-3-(4-fluorophenyl)-6-methoxybenzo[b]thiophene 1-oxide(2 g, 5.7 mmol) was added in small portions. After the mixture was stirred for 1 h, ethyl acetate and water were added, and the organic layer was washed several times with water and then dried over Na₂SO₄. The residue was titrated with hexane/ethyl acetate (10:1, v/v) and filtered to yield 2.47 g (89%) of desired product.

3-(4-fluorophenyl)-6-methoxy-2-(4-methoxyphenoxy)benzo[b]thiophene. LiAlH₄ (0.27 g, 7.2 mmol) was added in small portions to a solution of 3-(4-fluorophenyl)-6-methoxy-2-(4-methoxyphenoxy)benzo[b]thiophene 1-oxide (2.37 g, 4.8 mmol) in 180 mL of anhydrous THF under argon at 0° C. After the mixture was stirred for 30 min, the reaction was quenched by the slow addition of 4 mL of 2.0 MNaOH. The mixture was stirred vigorously for 30 min, and a minimal amount of 2.0 M NaOH was added to dissolve salts. The mixture was then partitioned between water and ethanol/ethyl acetate (1:9, v/v). The aqueous layer was isolated and then extracted several times with ethanol/ethyl acetate (1:9, v/v). The organic layers were combined, dried over anhydrous Na₂SO₄, concentrated in vacuo to an oil, and then purified by flash chromatography to give 1.2 g (67%) of desired product.

3-(4-fluorophenyl)-2-(4-hydroxyphenoxy)benzo[b]thiophen-6-ol (TTC-352). 3-(4-fluorophenyl)-6-methoxy-2-(4-methoxyphenoxy)benzo[b]thiophene(1.5 g, 2.9 mmol) was dissolved in 150 mL of anhydrous CH2Cl2 and cooled to 0° C. BBr₃ (1.0 M in CH2C2, 11.6 mL, 11.6 mmol) was added to this solution followed by stirring at 0° C. for 4 h. The reaction was quenched by saturated NaHCO₃(100 mL) and cooled to 0° C. The aqueous layer was isolated and extracted with methanol/ethyl acetate(5:95, v/v) (3_100 mL). The organic extracts were combined, dried over anhydrous Na2SO4, concentrated in vacuo, and then purified by flash chromatography [SiO2, CH2Cl2/MeOH (8:1, v/v)] to obtain 1.1 g (75%) desired product. ¹H NMR (400 MHz, acetone d6) δ (ppm) 6.84 (m, 2H), 6.97 (dd, 8.9 Hz, 2.2 Hz, 1H), 7.02 (m, 2H), 7.24 (m, 2H)), 7.28 (d, 2.2 Hz, 1H), 7.47 (d, 8.9 Hz, 1H), 7.61 (m, 2H)³C NMR (100 MHz acetone d6) δ (ppm) 162.84, 155.94, 155.02, 153.81, 152.35, 135.21, 132.28, 132.20, 130.90, 130.32, 123.70, 120.81, 119.67, 119.66, 116.95, 116.95, 116.39, 116.17, 115.52, 109.00.

4-((3-(4-fluorophenyl)-6-methoxybenzo[b]thiophen-2-yl)oxy)phenol (Monomethoxyl-TTC-352). Made from general procedure as TTC-352. ¹H NMR (400 MHz, Acetone d6) δ=7.62 (m, 2H), 7.52 (d, 8.9 Hz, 1H), 7.41 (d, 2.3 Hz, 1H), 7.25 (t, 8.9 Hz, 2H), 7.02 (dd, 9.0 Hz, 2.6, 3H), 6.83 (d, 9.0 Hz, 2H), 3.86 (s, 3H). ³C NMR (100 MHz acetone d6) δ (ppm) 161.95, 157.52, 154.09, 153.58, 151.34, 134.15, 131.34, 131.26, 130.71, 129.25, 122.60, 119.70, 118.79, 118.79, 116.00, 115.91, 115.46, 115.24, 114.20, 105.89, 55.04.

7. REFERENCES

1. Dempsey E C, Newton A C, Mochly-Rosen D, Fields A P, Reyland M E, Insel P A, et al. Protein kinase C isozymes and the regulation of diverse cell responses. American Journal of Physiology—Lung Cellular and Molecular Physiology. 2000; 279:L429-L38.
2. Mackay H J, Twelves C J. Protein kinase C: a target for anticancer drugs? Endocrine-Related Cancer. 2003; 10:389-96.
3. Assender J W, Gee J M W, Lewis I, Ellis I O, Robertson J F R, Nicholson R I. Protein kinase C isoform expression as a predictor of disease outcome on endocrine therapy in breast cancer. Journal of Clinical Pathology. 2007; 60:1216-21.
4. Tonetti D A, Morrow M, Kidwai N, Gupta A, Badve S. Elevated protein kinase C alpha expression may be predictive of tamoxifen treatment failure. Br J Cancer. 2003; 88:1400-2.
5. Lonne G, Cornmark L, Zahirovic I, Landberg G, Jirstrom K, Larsson C. PKCalpha expression is a marker for breast cancer aggressiveness. Molecular Cancer. 2010; 9:76.
6. Tonetti D A, Chisamore M J, Grdina W, Schurz H, Jordan V C. Stable transfection of protein kinase C alpha cDNA in hormone-dependent breast cancer cell lines. Br J Cancer. 2000; 83:782-91.
7. Chisamore M J, Ahmed Y, Bentrem D J, Jordan V C, Tonetti D A. Novel Antitumor Effect of Estradiol in Athymic Mice Injected with a T47D Breast Cancer Cell Line Overexpressing Protein Kinase Calpha. Clinical Cancer Research. 2001; 7:3156-65.
8. Yao K, Lee E-S, Bentrem D J, England G, Schafer J I M, O, ÄôRegan R M, et al. Antitumor Action of Physiological Estradiol on Tamoxifen-stimulated Breast Tumors Grown in Athymic Mice. Clinical Cancer Research. 2000; 6:2028-36.
9. Kennedy B J. Massive estrogen administration in premenopausal women with metastatic breast cancer. Cancer. 1962; 15:641-8.
10. Ingle J N, Ahmann D L, Green S J, Edmonson J H, Bisel H F, Kvols L K, et al. Randomized Clinical Trial of Diethylstilbestrol versus Tamoxifen in Postmenopausal Women with Advanced Breast Cancer. New England Journal of Medicine. 1981; 304:16-21.
11. White B P, Molloy M E, Zhao H, Zhang Y, Tonetti D A. Raloxifene and estradiol-induced tumor regression in tamoxifen-resistant T47D:A18/PKCα is accompanied by ERα translocation to extranuclear sites (submitted). Molecular Cancer Research. 2012.
12. Abdelhamid R, Luo J, Vandevrede L, Kundu I, Michalsen B, Litosh V A, et al. Benzothiophene Selective Estrogen Receptor Modulators Provide Neuroprotection by a novel GPR30-dependent Mechanism. ACS Chem Neurosci. 2011; 2:256-68.
13. Catherino W H, Jordan V C. Increasing the number of tandem estrogen response elements increases the estrogenic activity of a tamoxifen analogue. Cancer Letters. 1995; 92:39-47.
14. O'Regan R M, Cisneros A, England G M, Chatterton R, Dragan Y P. Effects of the Antiestrogens Tamoxifen, Toremifene, and ICI 182,780 on Endometrial Cancer Growth. Journal of the National Cancer Institute. 1998; 90:1552-8.
15. Zhang Y, Zhao H, Asztalos S, Chisamore M, Sitabkhan Y, Tonetti D A. Estradiol-Induced Regression in T47D: A18/PKCα Tumors Requires the Estrogen Receptor and Interaction with the Extracellular Matrix. Molecular Cancer Research. 2009; 7:498-510.
16. Overk C R, Peng K W, Asghodom R T, Kastrati I, Lantvit D D, Qin Z, et al. Structure-activity relationships for a family of benzothiophene selective estrogen receptor modulators including raloxifene and arzoxifene. ChemMedChem. 2007; 2:1520-6.
17. Qin Z, Kastrati I, Chandrasena R E, Liu H, Yao P, Petukhov P A, et al. Benzothiophene selective estrogen receptor modulators with modulated oxidative activity and receptor affinity. J Med Chem. 2007; 50:2682-92.
18. Yu B, Dietz B M, Dunlap T, Kastrati I, Lantvit D D, Overk C R, et al. Structural modulation of reactivity/activity in design of improved benzothiophene selective estrogen receptor modulators: induction of chemopreventive mechanisms. Mol Cancer Ther. 2007; 6:2418-28.
19. Qin Z, Kastrati I, Ashgodom R T, Lantvit D D, Overk C R, Choi Y, et al. Structural modulation of oxidative metabolism in design of improved benzothiophene selective estrogen receptor modulators. Drug Metab Dispos. 2009; 37:161-9.
20. Snyder K R, Sparano N, Malinowski J M. Raloxifene hydrochloride. Am J Health Syst Pharm. 2000; 57:1669-75; quiz 76-8.
21. Hochner-Celnikier D. Pharmacokinetics of raloxifene and its clinical application. Eur J Obstet Gynecol Reprod Biol. 1999; 85:23-9.
22. Palkowitz A D, Glasebrook A L, Thrasher K J, Hauser K L, Short L L, Phillips D L, et al. Discovery and synthesis of [6-hydroxy-3-[4-[2-(1-piperidinyl)ethoxy]phenoxy]-2-(4-hydroxyphenyl)]benzo[b]thiophene: a novel, highly potent, selective estrogen receptor modulator. J Med Chem. 1997; 40:1407-16.
23. Suh N, Glasebrook A L, Palkowitz A D, Bryant H U, Burris L L, Starling J J, et al. Arzoxifene, a new selective estrogen receptor modulator for chemoprevention of experimental breast cancer. Cancer Res. 2001; 61:8412-5.
24. Burke T W, Walker C L. Arzoxifene as therapy for endometrial cancer. Gynecol Oncol. 2003; 90:S40-6.
25. Buzdar A, O'Shaughnessy J A, Booser D J, Pippen J E, Jr., Jones S E, Munster P N, et al. Phase II, randomized, double-blind study of two dose levels of arzoxifene in patients with locally advanced or metastatic breast cancer. J Clin Oncol. 2003; 21:1007-14.
26. Liu H, Liu J, van Breemen R B, Thatcher GRJ, Bolton J L. Bioactivation of the selective estrogen receptor modulator desmethylated arzoxifene to quinoids: 4'-fluoro substitution prevents quinoid formation. Chem Res Toxicol. 2005; 18:162-73.
27. Liu H, Bolton J L, Thatcher G R J. Chemical modification modulates estrogenic activity, oxidative reactivity, and metabolic stability in 4'F-DMA, a new benzothiophene selective estrogen receptor modulator. Chem Res Toxicol. 2006; 19:779-87.
28. Fisher B, Costantino J P, Redmond C K, Fisher E R, Wickerham D L, Cronin W M, et al. Endometrial Cancer in Tamoxifen-Treated Breast Cancer Patients: Findings From the National Surgical Adjuvant Breast and Bowel Project (NSABP) B-14. Journal of the National Cancer Institute. 1994; 86:527-37.
29. Grese T A, Sluka J P, Bryant H U, Cullinan G J, Glasebrook A L, Jones C D, et al. Molecular determinants of tissue selectivity in estrogen receptor modulators. Proc Nat Acad Sci USA. 1997; 94:14105-10.
30. Grese T A, Cho S, Finley D R, Godfrey A G, Jones C D, Lugar C W, 3rd, et al. Structure-activity relationships of selective estrogen receptor modulators: modifications to the 2-arylbenzothiophene core of raloxifene. J Med Chem. 1997; 40:146-67.
31. Black L J, Sato M, Rowley E R, Magee D E, Bekele A, Williams D C, et al. Raoxifene (LY139481 HCl) prevents bone loss and reduces serum cholesterol without causing uterine hypertrophy in ovariectomized rats. J Clin Invest. 1994; 93:63-9.
32. Fuchs-Young R, Glasebrook A L, Short L L, Draper M W, Rippy M K, Cole H W, et al. Raloxifene is a tissue-selective agonist/antagonist that functions through the estrogen receptor. Ann NY Acad Sci. 1995; 761:355-60.
33. Ellis M J, Gao F, Dehdashti F, Jeffe D B, Marcom P K, Carey L A, et al. Lower-Dose vs High-Dose Oral Estradiol Therapy of Hormone Receptor-Positive, Aromatase Inhibitor-Resistant Advanced Breast Cancer. JAMA: The Journal of the American Medical Association. 2009; 302: 774-80.
34. Lenning P E, Taylor P D, Anker G, Iddon J, Wie L, Jorgensen L-M, et al. High-dose estrogen treatment in postmenopausal breast cancer patients heavily exposed to endocrine therapy. Breast Cancer Research and Treatment. 2001; 67:111-6.
35. Kelly M J, Levin E R. Rapid actions of plasma membrane estrogen receptors. Trends in Endocrinology and Metabolism. 2001; 12:152-6.
36. Song R X-D, McPherson R A, Adam L, Bao Y, Shupnik M, Kumar R, et al. Linkage of Rapid Estrogen Action to MAPK Activation by ER(E-Shc Association and Shc Pathway Activation. Molecular Endocrinology. 2002; 16:116-27.
37. Castoria G, Migliaccio A, Bilancio A, Di Domenico M, de Falco A, Lombardi M, et al. PI3-kinase in concert with Src promotes the S-phase entry of oestradiol-stimulated MCF-7 cells. EMBO J. 2001; 20:6050-9.
38. Pietras R J, Marquez-Garban D C. Membrane-Associated Estrogen Receptor Signaling Pathways in Human Cancers. Clinical Cancer Research. 2007; 13:4672-6.
39. Tran C, Ouk S, Clegg N J, Chen Y, Watson P A, Arora V, et al. Development of a Second-Generation Antiandrogen for Treatment of Advanced Prostate Cancer. Science. 2009; 324:787-90.

40. Clegg N J, Wongvipat J, Joseph J D, Tran C, Ouk S, Dilhas A, et al. ARN-509: A Novel Antiandrogen for Prostate Cancer Treatment. Cancer Research. 2012; 72:1494-503.
41. Ingle J. Estrogen as therapy for breast cancer. Breast Cancer Res. 2002; 4:133-6.
42. Song R X D, Santen R J. Apoptotic action of estrogen. Apoptosis. 2003; 8:55-60.
43. Ingle J N. Sequencing of Endocrine Therapy in Postmenopausal Women with Advanced Breast Cancer. Clinical Cancer Research. 2004; 10:362s-7s.
44. Jordan V C, Obiorah I, Fan P, Kim H R, Ariazi E, Cunliffe H, et al. The St. Gallen Prize Lecture 2011: Evolution of long-term adjuvant anti-hormone therapy: consequences and opportunities. The Breast. 2011; 20, Supplement 3:S1-S11.
45. Peethambaram P P, Ingle J N, Suman V J, Hartmann L C, Loprinzi C L. Randomized trial of diethylstilbestrol vs. tamoxifen in postmenopausal women with metastatic breast cancer. An updated analysis. Breast Cancer Research and Treatment. 1999; 54:117-22.
46. Osipo C, Gajdos C, Cheng D, Jordan V C. Reversal of tamoxifen resistant breast cancer by low dose estrogen therapy. The Journal of Steroid Biochemistry and Molecular Biology. 2005; 93:249-56.
47. Osipo C, Gajdos C, Liu H, Chen B, Jordan V C. Paradoxical Action of Fulvestrant in Estradiol-Induced Regression of Tamoxifen-Stimulated Breast Cancer. Journal of the National Cancer Institute. 2003; 95:1597-608.
48. Liu H, Lee E-S, Gajdos C, Pearce S T, Chen B, Osipo C, et al. Apoptotic Action of 17β-Estradiol in Raloxifene-Resistant MCF-7 Cells In Vitro and In Vivo. Journal of the National Cancer Institute. 200395:1586-97.
49. Santen R J, Song R X, Zhang Z, Yue W, Kumar R. Adaptive Hypersensitivity to Estrogen. Clinical Cancer Research. 2004; 10:337s-45s.
50. Song R X-D, Mor G, Naftolin F, McPherson R A, Song J, Zhang Z, et al. Effect of Long-Term Estrogen Deprivation on Apoptotic Responses of Breast Cancer Cells to 17β-Estradiol. Journal of the National Cancer Institute. 2001; 93:1714-23.
51. Lewis J S, Osipo C, Meeke K, Jordan V C. Estrogen-induced apoptosis in a breast cancer model resistant to long-term estrogen withdrawal. The Journal of Steroid Biochemistry and Molecular Biology. 2005; 94:131-41.
52. Shim W-S, Conaway M, Masamura S, Yue W, Wang J-P, Kumar R, et al. Estradiol Hypersensitivity and Mitogen-Activated Protein Kinase Expression in Long-Term Estrogen Deprived Human Breast Cancer Cells in Vivo. Endocrinology. 2000; 141:396-405.
53. Liu, H.; Qin, Z.; Thatcher, G. R.; Bolton, J. L. Uterine peroxidase-catalyzed formation of diquinone methides from the selective estrogen receptor modulators raloxifene and desmethylated arzoxifene. Chem Res Toxicol 2007, 20, 1676-84.

What is claimed is:

1. A method for treatment of an estrogen-related medical disorder, the method comprising administering to a subject in need of such treatment a composition comprising a therapeutically effective amount of at least one compound of formula (I)

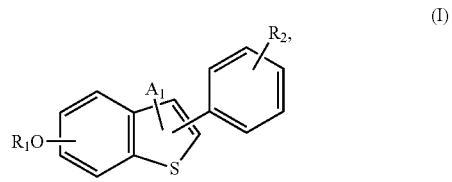

or a pharmaceutically acceptable salt thereof, wherein $R_1$ is selected from the group consisting of hydrogen, alkyl, $-SO_3R^{x1}$, $-PO_3R^{y1}R^{z1}$, and $-C(=O)R^a$;

$R_2$ is selected from the group consisting of halo and $-OR_3$;

$R_3$ is selected from the group consisting of hydrogen, alkyl, $-SO_3R^{x1}$, $-PO_3R^{y1}R^{z1}$, and $-C(=O)R^a$;

$A_1$ is $-OR^{b2}$ or $-C(=O)R^{b3}$;

$R^{b3}$ is selected from the group consisting of cycloalkyl, and phenyl substituted with 1, 2, or 3 halo;

$R^{b2}$ is selected from the group consisting of alkyl, cycloalkyl, and phenyl substituted with 1, 2, or 3 substituents independently selected from the group consisting of halo and $-OR_4$;

$R_4$ is selected from the group consisting of hydrogen, alkyl, $-SO_3R^{x1}$, $-PO_3R^{y1}R^{z1}$, and $-C(=O)R^a$;

R, at each occurrence, is independently selected from the group consisting of $-OH$ and alkyl; and $R^{x1}$, $R^{y1}$ and $R^{z1}$ are, at each occurrence, independently selected from the group consisting of hydrogen and a pharmaceutically acceptable cation;

provided that the compound of formula (I) contains at least one group selected from $-OR_3$ and $-OR_4$;

provided that 2-(4-fluorophenyl)-3-(4-hydroxyphenoxy)benzo[b]thiophen-6-ol is excluded from the compound of formula (I), wherein the estrogen-related medical disorder is Alzheimer's Disease.

2. The method of claim 1, wherein the at least one compound of formula (I) is 3-(4-fluorophenyl)-2-(4-hydroxyphenoxy)benzo[b]thiophen-6-ol;

or a pharmaceutically acceptable thereof.

3. A method for treatment of an estrogen-related medical disorder, the method comprising administering to a subject in need of such treatment a composition comprising a therapeutically effective amount of at least one compound of formula (II)

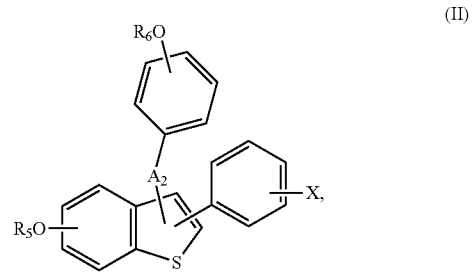

or a pharmaceutically acceptable salt thereof, wherein

A₂ is —O— or —C(=O)—;

$R_5$ and $R_6$ are each independently selected from the group consisting of hydrogen, alkyl, —SO₃$R^{x2}$, —PO₃$R^{y2}R^{y3}$, and —C(=O)$R^c$;

$R^c$ is selected from the group consisting of —OH and alkyl;

$R^{x2}$, $R^{y2}$ and $R^{z2}$ are each independently selected from the group consisting of hydrogen and a pharmaceutically acceptable cation; and X is halogen or trifluoromethyl;

provided that 2-(4-fluorophenyl)-3-(4-hydroxyphenoxy)benzo[b]thiophen-6-ol is excluded from the compound of formula (II), wherein the estrogen-related medical disorder is Alzheimer's Disease.

4. The method of claim 3, wherein the at least one compound of formula (II) is 3-(4-fluorophenyl)-2-(4-hydroxyphenoxy)benzo[b]thiophen-6-ol or a pharmaceutically acceptable thereof.

5. The method of claim 1, wherein the compound has formula (I-vii)

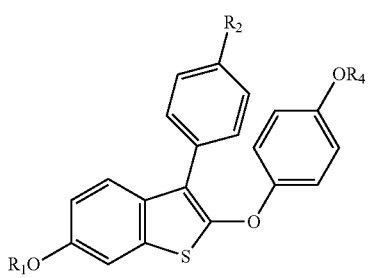

(I-vii)

wherein $R_1$ is selected from the group consisting of hydrogen, alkyl, —SO₃$R^{x1}$, —PO₃$R^{y1}R^{z1}$, and —C(=O)$R^a$;

$R_2$ is selected from the group consisting of halo and —OR₃;

$R_3$ is selected from the group consisting of hydrogen, alkyl, —SO₃$R^{x1}$, —PO₃$R^{y1}R^{z1}$, and —C(=O)$R^a$;

$R_4$ is selected from the group consisting of hydrogen, alkyl, —SO₃$R^{x1}$, —PO₃$R^{y1}R^{z1}$, and —C(=O)$R^a$;

$R^a$, at each occurrence, is independently selected from the group consisting of —OH and alkyl; and $R^{x1}$, $R^{y1}$ and $R^{z1}$ are, at each occurrence, independently selected from the group consisting of hydrogen and a pharmaceutically acceptable cation.

6. The method of claim 5, wherein the compound has formula (I-viii),

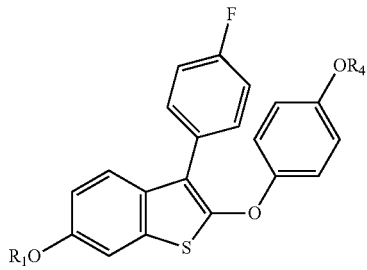

(I-viii)

wherein $R_1$ and $R_4$ are as defined in claim 5.

7. The method of claim 5, wherein the compound has formula (I-ix),

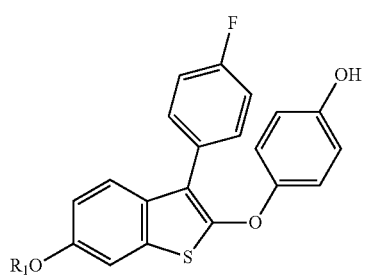

(I-ix)

wherein $R_1$ is as defined in claim 5.

8. The method of claim 5, wherein the compound has formula (I-x),

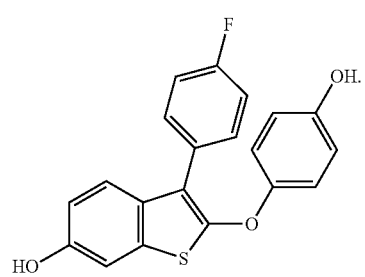

(I-x)

* * * * *